(12) United States Patent
Solsberg et al.

(10) Patent No.: US 8,894,653 B2
(45) Date of Patent: Nov. 25, 2014

(54) PERCUTANEOUS TISSUE EXCISION DEVICES AND METHODS

(71) Applicant: Vertos Medical Inc., Aliso Viejo, CA (US)

(72) Inventors: Murray David Solsberg, Englewood, CO (US); Donald Schomer, Englewood, CO (US); Bryce Way, San Jose, CA (US); Minh Tran, Fountain Valley, CA (US)

(73) Assignee: Vertos Medical, Inc., Aliso Viejo, CA (US)

( * ) Notice: Subject to any disclaimer, the term of this patent is extended or adjusted under 35 U.S.C. 154(b) by 0 days.

(21) Appl. No.: 14/019,135

(22) Filed: Sep. 5, 2013

(65) Prior Publication Data
US 2014/0005671 A1 Jan. 2, 2014

Related U.S. Application Data

(63) Continuation of application No. 11/461,045, filed on Jul. 31, 2006.

(60) Provisional application No. 60/747,166, filed on May 12, 2006, provisional application No. 60/704,224, filed on Jul. 29, 2005.

(51) Int. Cl.
*A61B 17/00* (2006.01)
*A61B 17/32* (2006.01)
(Continued)

(52) U.S. Cl.
CPC ..... *A61B 17/1671* (2013.01); *A61B 17/320016* (2013.01); *A61M 5/007* (2013.01); *A61B*
(Continued)

(58) Field of Classification Search
USPC .................................................. 606/205–211
See application file for complete search history.

(56) References Cited

U.S. PATENT DOCUMENTS

| 1,493,240 A | 5/1924 | Bohn |
| 2,670,519 A | 3/1954 | Recklitis |

(Continued)

FOREIGN PATENT DOCUMENTS

| GB | 2177307 A1 | 1/1987 |
| WF | WO 96/29936 A1 | 10/1996 |

(Continued)

OTHER PUBLICATIONS

Basu, S., "Mild Procedure: Single-site Prospective IRB Study" *Clinical Journal of Pain*, [online], www.clinicalpain.com, Ahead-of-Print publication, doi: 10.1097/AJP.0b013e31822bb344, 2011 (5 pages). Final publication in vol. 28, Issue 3, pp, 254-258, Mar./Apr. 2012.

(Continued)

*Primary Examiner* — Kevin T Truong
*Assistant Examiner* — Christine Nelson
(74) *Attorney, Agent, or Firm* — Finnegan, Henderson, Farabow, Garrett & Dunner, LLP

(57) ABSTRACT

A device for percutaneously excising tissue. In an embodiment, the device comprises an outer tubular. In addition, the device comprises an inner tubular slidingly received within the outer tubular, wherein the inner tubular has a distal end including an upper member and a lower member. Further, the device includes an open position with the distal end fully extended from the outer tubular, and a closed position with the distal end disposed within the outer tubular, wherein the upper member is biased away from the lower member and is disposed at an open angle $\theta_O$ relative to the lower member when the device is in the opened position.

35 Claims, 11 Drawing Sheets

(51) Int. Cl.
*A61M 5/00* (2006.01)
*A61B 10/02* (2006.01)
*A61B 17/16* (2006.01)
*A61B 17/064* (2006.01)
*A61B 17/29* (2006.01)
*A61B 10/06* (2006.01)
*A61B 17/295* (2006.01)

(52) U.S. Cl.
CPC .............. 10/0275 (2013.01); *A61B 2017/0646* (2013.01); *A61B 2017/0647* (2013.01); *A61B 2017/2925* (2013.01); *A61B 10/06* (2013.01); *A61B 2017/00261* (2013.01); *A61B 2017/00336* (2013.01); *A61B 2017/32004* (2013.01); *A61B 2017/2911* (2013.01); A61B 17/1608 (2013.01); *A61B 17/29* (2013.01); *A61B 2017/00685* (2013.01); *A61B 2017/320064* (2013.01); *A61B 17/295* (2013.01)
USPC ................................ 606/79; 606/83; 606/205

(56) References Cited

U.S. PATENT DOCUMENTS

| | | | |
|---|---|---|---|
| 3,001,522 A | 9/1961 | Silverman | |
| 3,628,524 A | 12/1971 | Jamshidi | |
| 3,732,858 A | 5/1973 | Banko | |
| 3,893,445 A | 7/1975 | Hofsess | |
| 3,929,123 A | 12/1975 | Jamshidi | |
| 3,945,372 A | 3/1976 | Milan et al. | |
| 4,103,690 A | 8/1978 | Harris | |
| 4,174,715 A | 11/1979 | Hasson | |
| 4,200,111 A | 4/1980 | Harris | |
| 4,201,213 A | 5/1980 | Townsend | |
| 4,283,129 A | 8/1981 | Bennick | |
| 4,522,206 A | 6/1985 | Whipple et al. | |
| 4,535,773 A | 8/1985 | Yoon | |
| 4,603,694 A | 8/1986 | Wheeler | |
| 4,682,606 A | 7/1987 | DeCaprio | |
| 4,708,147 A | 11/1987 | Haaga | |
| 4,733,663 A | 3/1988 | Farley | |
| 4,777,948 A | 10/1988 | Wright | |
| 4,801,293 A | 1/1989 | Jackson | |
| 4,811,734 A | 3/1989 | McGurk-Burleson et al. | |
| 4,834,729 A | 5/1989 | Sjostrom | |
| 4,844,064 A | 7/1989 | Thimsen et al. | |
| 4,850,354 A | 7/1989 | McGurk-Burleson et al. | |
| 4,867,157 A | 9/1989 | McGurk-Burleson et al. | |
| 4,931,059 A | 6/1990 | Markham | |
| 4,991,600 A | 2/1991 | Taylor | |
| 4,994,072 A | 2/1991 | Bhate et al. | |
| 5,026,375 A | 6/1991 | Linovitz et al. | |
| 5,026,386 A | 6/1991 | Michelson | |
| 5,040,542 A | 8/1991 | Gray | |
| 5,108,403 A | 4/1992 | Stern | |
| 5,127,916 A | 7/1992 | Spencer et al. | |
| 5,172,702 A | 12/1992 | Leigh et al. | |
| 5,180,393 A | 1/1993 | Commarmond | |
| 5,190,759 A | 3/1993 | Lindblad et al. | |
| 5,215,105 A | 6/1993 | Kizelshteyn et al. | |
| 5,226,910 A | 7/1993 | Kajiyama et al. | |
| 5,269,785 A | 12/1993 | Bonutti | |
| 5,281,230 A | 1/1994 | Heidmueller | |
| 5,286,255 A | 2/1994 | Weber | |
| 5,290,303 A | 3/1994 | Pingleton et al. | |
| 5,300,045 A | 4/1994 | Plassche, Jr. | |
| 5,320,110 A | 6/1994 | Wang | |
| 5,354,266 A | 10/1994 | Snoke | |
| 5,366,477 A | 11/1994 | Lemarie, III et al. | |
| 5,373,854 A | 12/1994 | Kolozsi | |
| 5,385,570 A | 1/1995 | Chin et al. | |
| 5,429,136 A | 7/1995 | Milo et al. | |
| 5,429,138 A | 7/1995 | Jamshidi | |
| 5,439,464 A | 8/1995 | Shapiro | |
| 5,451,227 A | 9/1995 | Michaelson | |
| 5,458,112 A | 10/1995 | Weaver | |
| 5,462,062 A | 10/1995 | Rubinstein et al. | |
| 5,484,437 A | 1/1996 | Michelson | |
| 5,496,269 A | 3/1996 | Snoke | |
| 5,514,379 A | 5/1996 | Weissleder et al. | |
| 5,522,825 A | 6/1996 | Kropf et al. | |
| 5,531,749 A | 7/1996 | Michelson | |
| 5,538,008 A | 7/1996 | Crowe | |
| 5,540,693 A | 7/1996 | Fisher | |
| 5,562,102 A | 10/1996 | Taylor | |
| 5,569,258 A | 10/1996 | Gambale | |
| 5,569,284 A | 10/1996 | Young et al. | |
| 5,578,030 A | 11/1996 | Levin | |
| 5,582,618 A | 12/1996 | Chin et al. | |
| 5,595,186 A | 1/1997 | Rubinstein et al. | |
| 5,613,972 A | 3/1997 | Lee et al. | |
| 5,637,096 A | 6/1997 | Yoon | |
| 5,638,827 A | 6/1997 | Palmer et al. | |
| 5,645,075 A | 7/1997 | Palmer et al. | |
| 5,649,547 A | 7/1997 | Ritchart et al. | |
| 5,681,337 A | 10/1997 | Bray, Jr. | |
| 5,705,485 A | 1/1998 | Cini et al. | |
| 5,709,697 A | 1/1998 | Ratcliff et al. | |
| 5,718,237 A | 2/1998 | Haaga | |
| 5,730,754 A | 3/1998 | Obenchain | |
| 5,735,865 A | 4/1998 | Schaumann et al. | |
| 5,759,185 A | 6/1998 | Grinberg | |
| 5,772,597 A | 6/1998 | Goldberger et al. | |
| 5,775,333 A | 7/1998 | Burbank et al. | |
| 5,776,075 A | 7/1998 | Palmer | |
| 5,782,849 A | 7/1998 | Miller | |
| 5,792,044 A | 8/1998 | Foley et al. | |
| 5,797,936 A | 8/1998 | Kleihues | |
| 5,797,939 A | 8/1998 | Yoon | |
| 5,797,958 A | 8/1998 | Yoon | |
| 5,823,970 A | 10/1998 | Terwilliger | |
| 5,827,289 A | 10/1998 | Reiley et al. | |
| 5,827,305 A | 10/1998 | Gordon | |
| 5,836,948 A | 11/1998 | Zucherman et al. | |
| 5,840,338 A | 11/1998 | Roos et al. | |
| 5,843,121 A | 12/1998 | Yoon | |
| 5,853,366 A | 12/1998 | Dowlatshahi | |
| 5,857,996 A | 1/1999 | Snoke | |
| 5,860,991 A | 1/1999 | Klein et al. | |
| 5,868,745 A | 2/1999 | Alleyne | |
| 5,871,453 A | 2/1999 | Banik et al. | |
| 5,873,886 A | 2/1999 | Larsen et al. | |
| 5,879,353 A | 3/1999 | Terry | |
| 5,879,365 A | 3/1999 | Whitfield et al. | |
| 5,916,858 A | 6/1999 | Kim et al. | |
| 5,925,050 A | 7/1999 | Howard, III | |
| 5,925,056 A | 7/1999 | Thomas et al. | |
| 5,931,855 A | 8/1999 | Buncke | |
| 5,954,739 A | 9/1999 | Bonutti | |
| 5,964,782 A | 10/1999 | Lafontaine et al. | |
| 5,980,525 A | 11/1999 | Bryant et al. | |
| 5,984,939 A | 11/1999 | Yoon | |
| 5,985,320 A | 11/1999 | Edwards et al. | |
| 6,010,493 A | 1/2000 | Snoke | |
| 6,019,765 A | 2/2000 | Thornhill et al. | |
| 6,022,362 A | 2/2000 | Lee et al. | |
| 6,053,877 A | 4/2000 | Banik et al. | |
| 6,083,237 A | 7/2000 | Huitema et al. | |
| 6,096,053 A | 8/2000 | Bates | |
| 6,110,127 A | 8/2000 | Suzuki | |
| 6,139,508 A * | 10/2000 | Simpson et al. | 600/564 |
| 6,139,608 A | 10/2000 | Woodbridge et al. | |
| 6,142,957 A | 11/2000 | Diamond et al. | |
| 6,142,997 A | 11/2000 | Michelson | |
| 6,214,010 B1 | 4/2001 | Farley et al. | |
| 6,221,006 B1 | 4/2001 | Dubrul et al. | |
| 6,241,747 B1 | 6/2001 | Ruff | |
| 6,258,093 B1 | 7/2001 | Edwards et al. | |
| 6,261,294 B1 | 7/2001 | Stihl et al. | |
| 6,261,582 B1 | 7/2001 | Needham et al. | |
| 6,264,087 B1 | 7/2001 | Whitman | |
| 6,264,617 B1 | 7/2001 | Bales et al. | |
| 6,268,405 B1 | 7/2001 | Yao et al. | |
| 6,273,862 B1 | 8/2001 | Privitera et al. | |

(56) References Cited

U.S. PATENT DOCUMENTS

| | | |
|---|---|---|
| 6,287,304 B1 | 9/2001 | Eggers et al. |
| 6,296,639 B1 | 10/2001 | Truckai et al. |
| 6,306,156 B1 | 10/2001 | Clark |
| 6,332,886 B1 | 12/2001 | Green et al. |
| 6,358,217 B1 | 3/2002 | Bourassa |
| 6,358,254 B1 | 3/2002 | Anderson |
| 6,371,968 B1 | 4/2002 | Kogasaka et al. |
| 6,375,659 B1 | 4/2002 | Erbe et al. |
| 6,419,684 B1 | 7/2002 | Heisler et al. |
| 6,423,332 B1 | 7/2002 | Huxel et al. |
| 6,425,859 B1 | 7/2002 | Foley et al. |
| 6,428,486 B2 | 8/2002 | Ritchart et al. |
| 6,428,498 B2 | 8/2002 | Uflacker |
| 6,443,910 B1 | 9/2002 | Krueger et al. |
| 6,454,767 B2 | 9/2002 | Alleyne |
| 6,464,682 B1 | 10/2002 | Snoke |
| 6,470,209 B2 | 10/2002 | Snoke |
| 6,478,805 B1 | 11/2002 | Marino et al. |
| 6,488,636 B2 | 12/2002 | Bryan et al. |
| 6,506,190 B1 | 1/2003 | Walshe |
| 6,514,256 B2 | 2/2003 | Zucherman et al. |
| 6,520,907 B1 | 2/2003 | Foley et al. |
| 6,530,933 B1 | 3/2003 | Yeung et al. |
| 6,533,795 B1 | 3/2003 | Tran et al. |
| 6,572,563 B2 | 6/2003 | Ouchi |
| 6,575,919 B1 | 6/2003 | Reiley et al. |
| 6,575,968 B1 | 6/2003 | Eggers et al. |
| 6,579,291 B1 | 6/2003 | Keith et al. |
| 6,599,310 B2 | 7/2003 | Leung et al. |
| 6,602,248 B1 | 8/2003 | Sharps et al. |
| 6,605,294 B2 | 8/2003 | Sawhney |
| 6,620,185 B1 | 9/2003 | Harvie et al. |
| 6,626,916 B1 | 9/2003 | Yeung et al. |
| 6,632,182 B1 | 10/2003 | Treat |
| 6,645,213 B2 | 11/2003 | Sand et al. |
| 6,652,558 B2 | 11/2003 | Patel et al. |
| 6,669,729 B2 | 12/2003 | Chin |
| 6,682,535 B2 | 1/2004 | Hoogland |
| 6,692,445 B2 | 2/2004 | Roberts et al. |
| 6,716,216 B1 | 4/2004 | Boucher et al. |
| 6,746,093 B2 | 6/2004 | Martinez |
| 6,746,451 B2 | 6/2004 | Middleton et al. |
| 6,772,012 B2 | 8/2004 | Ricart et al. |
| 6,783,534 B2 | 8/2004 | Mehdizadeh |
| 6,818,001 B2 | 11/2004 | Wulfman et al. |
| 6,852,095 B1 | 2/2005 | Ray |
| 6,858,229 B1 | 2/2005 | Hubbell et al. |
| 6,925,323 B2 | 8/2005 | Snoke |
| 7,008,433 B2 | 3/2006 | Voellmicke et al. |
| 7,025,771 B2 | 4/2006 | Kuslich et al. |
| 7,041,050 B1 | 5/2006 | Ronald |
| 7,066,942 B2 | 6/2006 | Treace |
| 7,070,596 B1 | 7/2006 | Woloszko et al. |
| 7,101,382 B2 | 9/2006 | George et al. |
| 7,104,986 B2 | 9/2006 | Hovda et al. |
| 7,118,576 B2 | 10/2006 | Gitis et al. |
| 7,131,951 B2 | 11/2006 | Angel |
| 7,137,956 B2 | 11/2006 | Nishtalas et al. |
| 7,181,289 B2 | 2/2007 | Pflueger et al. |
| 7,189,206 B2 | 3/2007 | Quick et al. |
| 7,189,240 B1 | 3/2007 | Dekel |
| 7,201,722 B2 | 4/2007 | Krueger |
| 7,226,424 B2 | 6/2007 | Ritchart et al. |
| 7,276,032 B2 | 10/2007 | Hibner |
| 7,309,338 B2 | 12/2007 | Cragg |
| 7,322,978 B2 | 1/2008 | West |
| 7,329,402 B2 | 2/2008 | Unger et al. |
| 7,445,634 B2 | 11/2008 | Trieu |
| 7,942,830 B2 | 5/2011 | Solsberg et al. |
| 2001/0005778 A1 | 6/2001 | Ouchi |
| 2001/0044635 A1 | 11/2001 | Niizeki et al. |
| 2003/0009125 A1 | 1/2003 | Nita et al. |
| 2003/0050574 A1 | 3/2003 | Krueger |
| 2003/0077225 A1 | 4/2003 | Laurent et al. |
| 2003/0165555 A1 | 9/2003 | Ding et al. |
| 2003/0220650 A1 | 11/2003 | Major et al. |
| 2004/0049217 A1 | 3/2004 | Ross et al. |
| 2004/0059370 A1 | 3/2004 | Greene et al. |
| 2004/0138701 A1 | 7/2004 | Haluck |
| 2004/0210231 A1 | 10/2004 | Boucher et al. |
| 2005/0037079 A1 | 2/2005 | Son et al. |
| 2005/0038432 A1 | 2/2005 | Shaolian et al. |
| 2005/0070913 A1 | 3/2005 | Milbocker et al. |
| 2005/0075630 A1 | 4/2005 | Truckai et al. |
| 2005/0080441 A1 | 4/2005 | Dodge et al. |
| 2005/0137602 A1 | 6/2005 | Assell et al. |
| 2005/0163850 A1 | 7/2005 | Wong et al. |
| 2005/0197661 A1 | 9/2005 | Carrison et al. |
| 2005/0209610 A1 | 9/2005 | Carrison |
| 2005/0228403 A1 | 10/2005 | Ho et al. |
| 2005/0261692 A1 | 11/2005 | Carrison et al. |
| 2006/0030785 A1 | 2/2006 | Field et al. |
| 2006/0036211 A1 | 2/2006 | Solsberg et al. |
| 2006/0036271 A1 | 2/2006 | Schomer et al. |
| 2006/0036272 A1 | 2/2006 | Solsberg et al. |
| 2006/0089609 A1 | 4/2006 | Bleich et al. |
| 2006/0089633 A1 | 4/2006 | Bleich et al. |
| 2006/0089640 A1 | 4/2006 | Bleich et al. |
| 2006/0094976 A1 | 5/2006 | Bleich |
| 2006/0095028 A1 | 5/2006 | Bleich |
| 2006/0095059 A1 | 5/2006 | Bleich et al. |
| 2006/0100651 A1 | 5/2006 | Bleich |
| 2006/0122458 A1 | 6/2006 | Bleich |
| 2006/0122535 A1 | 6/2006 | Daum |
| 2006/0135882 A1 | 6/2006 | Bleich |
| 2006/0178682 A1 | 8/2006 | Boehlke |
| 2006/0184175 A1 | 8/2006 | Schomer et al. |
| 2006/0206115 A1 | 9/2006 | Schomer et al. |
| 2006/0206178 A1 | 9/2006 | Kim |
| 2006/0224160 A1 | 10/2006 | Trieu et al. |
| 2006/0235334 A1 | 10/2006 | Corvi et al. |
| 2006/0235422 A1 | 10/2006 | Keller |
| 2006/0235451 A1 | 10/2006 | Schomer et al. |
| 2006/0235452 A1 | 10/2006 | Schomer et al. |
| 2006/0264994 A1 | 11/2006 | Schomer et al. |
| 2007/0005084 A1 | 1/2007 | Clague et al. |
| 2007/0027464 A1 | 2/2007 | Way et al. |
| 2007/0055263 A1 | 3/2007 | Way et al. |
| 2007/0123888 A1 | 5/2007 | Bleich et al. |
| 2007/0123890 A1 | 5/2007 | Way et al. |
| 2007/0162061 A1 | 7/2007 | Way et al. |
| 2007/0198019 A1 | 8/2007 | Schomer et al. |
| 2007/0213735 A1 | 9/2007 | Saadat et al. |
| 2007/0225703 A1 | 9/2007 | Schmitz et al. |
| 2007/0260253 A1 | 11/2007 | Johnson et al. |
| 2008/0161809 A1 | 7/2008 | Schmitz et al. |
| 2008/0221383 A1 | 9/2008 | Way et al. |
| 2009/0036936 A1 | 2/2009 | Solsberg et al. |
| 2009/0118709 A1 | 5/2009 | Sand et al. |

FOREIGN PATENT DOCUMENTS

| | | |
|---|---|---|
| WO | WO 97/34536 A2 | 9/1987 |
| WO | WO 96/22056 A1 | 7/1996 |
| WO | WO 98/22022 | 5/1998 |
| WO | WO 98/40015 A2 | 9/1998 |
| WO | WO 00/46868 A1 | 8/2000 |
| WO | WO 01/08571 A1 | 2/2001 |
| WO | WO 01/82998 A2 | 11/2001 |
| WO | WO 02/078311 A2 | 10/2002 |
| WO | WO 2006/015302 A1 | 2/2006 |
| WO | WO 2006/044727 A2 | 4/2006 |
| WO | WO 2007/085628 A1 | 8/2007 |
| WO | WO 2007/113808 A1 | 10/2007 |
| WO | WO 2008/042793 A2 | 4/2008 |
| WO | WO 2008/070867 A2 | 6/2008 |
| WO | WO 2008/139260 A2 | 11/2008 |

OTHER PUBLICATIONS

Brown, L., "A Double-blind, Randomized, Prospective Study of Epidural Steroid Injection vs. The *mild*®, Procedure in Patients with Symptomatic Lumbar Spinal Stenosis" *Pain Practice*, 12(5):333-341 (2012).

(56) References Cited

OTHER PUBLICATIONS

Brunette, J. et al. "Comparative Rheology of Low- and Iso-Osrnolarity Contrast Agents at Different Temperatures," *Catheterization and Cardiovascular Interventions*, 71:78-83 (2008).

Chen, H. et al., "*mild* Procedure for Lumbar Decompression: A Review" *Pain Practice*, 13(2):146-153 (2013).

Chopko, B. et al., "MiDAS I (*mild®* Decompression Alternative to Open Surgery): A Preliminary Report of a Prospective, Multi-Center Clinical Study" *Pain Physician*, 13:369-378 (2010).

Chopko, B., "A novel method for treatment of lumbar spinal stenosis in high-risk surgical candidates: pilot study experience with percutaneous remodeling of ligamenturn flavum and lamina" *J. Neurosurg. Spine*, 14:46-50 (2011).

Chopko, B., "Long-term Results of Percutaneous Lumbar Decompression for LSS: Two-Year Outcomes" *Clinical Journal of Pain*, [onlilne]. Retrieved from: www.clinicalpain.com, Ahead-of-Print publication, doi: 10.1097/AJP.0b013e31827fb803, Feb. 26, 2013 (5 pages).

Deer, T., "Minimally Invasive Lumbar Decompression for Spinal Stenosis" *JNR*, 1(S1):29-32(2011).

Deer, T. et al., "New Image-Guided Ultra-Minimally Invasive Lumbar Decompression Method: The *mild®* Procedure" *Proceure Pain Physician*, 13:35-41 (2010).

Deer, T. et al., "Study of Percutaneous Lumbar Decompression and Treatment Algorithm for Patients Suffering from Neurogenic Claudication" *Pain Physician*, 15:451-460 (2012).

Deer, T., "Minimally invasive lumbar decompression for the treatment of spinal stenosis of the lumbar spine" *Pain Management*, 2(5):457-465 (2012).

European Communication issued in European Application No. 11150538.4-2310, dated Apr. 17, 2012.

European Office Action issued in Application No. 06800718.6 mailed on Mar. 8, 2010.

European Search Report issued in EP 08800718.6 mailed Oct. 28, 2009.

European Search Report issued in EP 08253596.4, mailed on Mar. 27, 2009.

European Search Report issued in EP 08253854.7, mailed on Apr. 4, 2009.

European Search Report issued in EP 08253854.6, mailed on Feb. 2, 2010.

European Search Report issued in EP 11150538.4, mailed on May 23, 2011.

Great Britain Search Report issued in GB 0821929.7, dated Mar. 2, 2009.

International Search Report and Written Opinion issued in PCT/US2006/30296, mailed on Jan. 11, 2008.

International Search Report and Written Opinion issued in PCT/US2006/30299, mailed on Aug. 3, 2007.

International Search Report and Written Opinion issued in PCT/US2006/30302, mailed on Jul. 3, 2008.

International Search Report and Written Opinion issued in PCT/US2006/43242, mailed on Sep. 18, 2007.

International Search Report and Written Opinion issued in PCT/US2007/68553, mailed on Sep. 11, 2008.

International Search Report issued in PCT/US2005/27216, mailed on Jan. 12, 2006.

International Search Report issued in PCT/US2008/53681, mailed on Jul. 29, 2008.

Levy, R. et al, "Systematic Safety Review and Meta-Analysis of Procedural Experience Using Percutaneous Access to Treat Symptomatic Lumbar Spina Stenosis" *Pain Medicine*, [online], http://onlinelibary.wiley.com/doi/10.1111/j.1526-4637.2012.01504.x, published online Nov. 8, 2012 (8 pages). Final publication in vol. 13, Issue 12, pp, 1554-1561, Dec. 2012.

Lingreen, R. et al., "Retrospective Review of Patient Self-Reported Improvement and Post-Procedure Findings for *mild®* (Minimally Invasive Lumbar Decompression)" *Pain Physician*, 13:555-560 (2010).

Mekhail, N, et al. "Functional and Patient Reported Outcomes in Symptomatic Lumbar Spinal Stenosis Following Percutaneous Decompression" *Pain Practice*, [online], http://onlinelibrary.wiley.com/doi/10.1111/j.1533-2500.2012.00565.x, published online Jun. 1, 2012 (9 pages). Final publication in vol. 12, Issue 6, pp. 417-425, Jul. 2012.

Mekhail, N. et al., "Long-Term Results of Percutaneous Lumbar Decompression mild® for Spinal Stenosis" *Pain Practice*, [online], http://onlinelibrary.wiley.com/doi/10.111/j.1533-2500.2011.00481.x, published online Jun. 16, 2011 (10 pages). Final publication in vol. 12, Issue 3, pp. 184-193, Mar. 2012.

Schomer, D. et al., "*mild®* Lumbar Decompression for the Treatment of Lumbar Spinal Stenosis" *The Neuroradiclogy Journal*, 24:620-626 (2011).

Wong, W., "*mild* Interlaminar Decompression for the Treatment of Lumbar Spinal Stenosis" *Clinical Journal of Pain*, 28(6):534-538 (2012).

Written Opinion issued in PCT/US2005/27216, mailed on Jan. 12, 2006.

\* cited by examiner

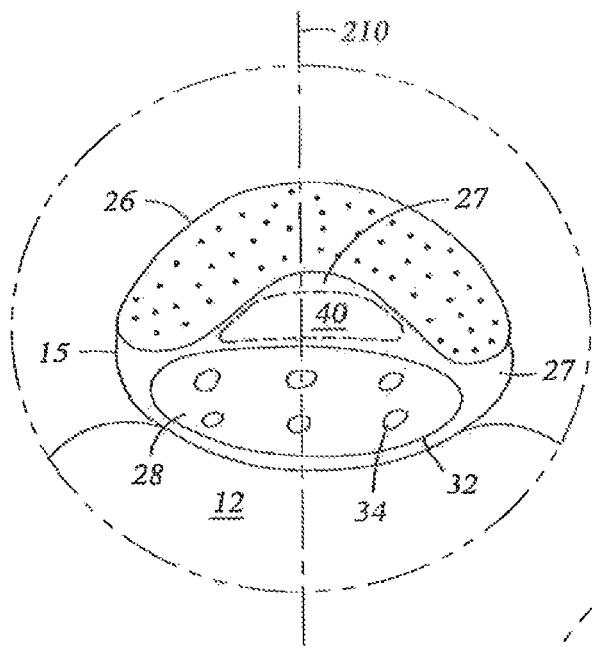
Fig. 3
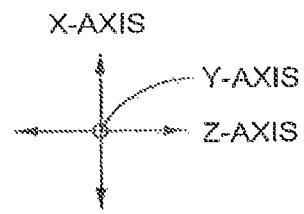
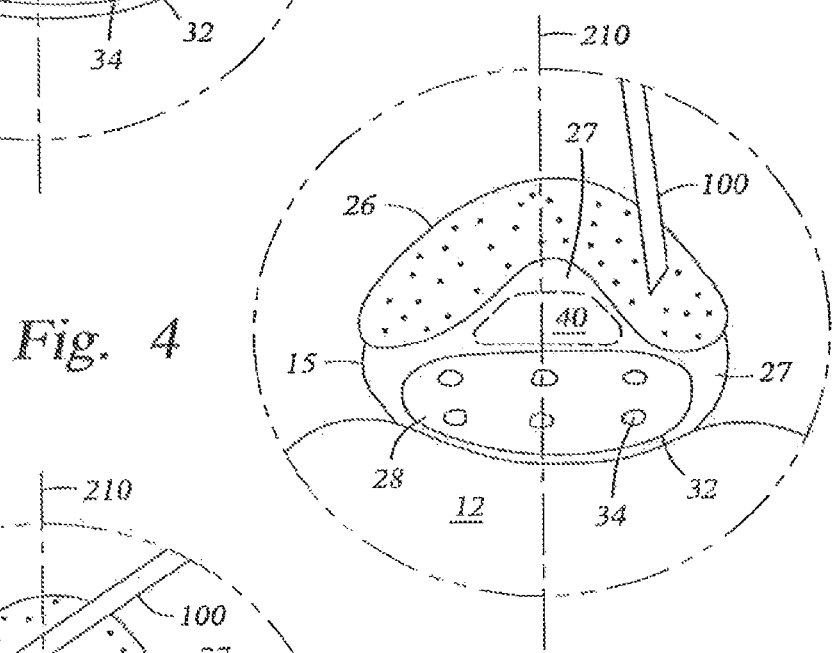
Fig. 4
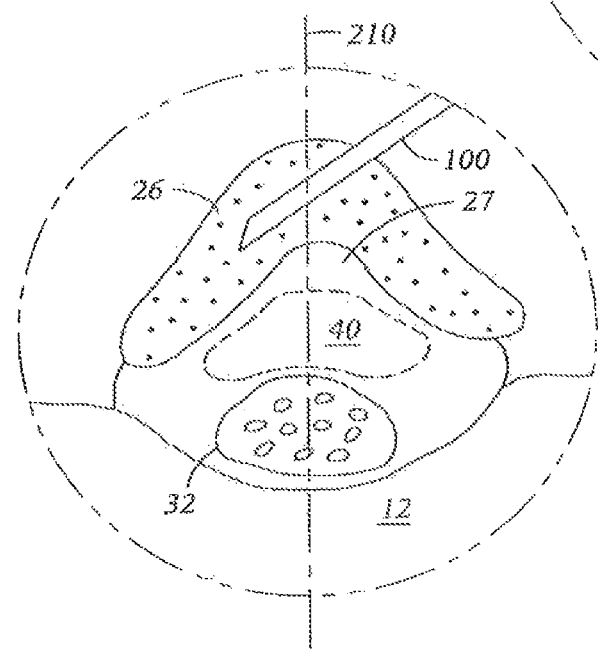
Fig. 5

PERCUTANEOUS TISSUE EXCISION DEVICES AND METHODS

CROSS-REFERENCE TO RELATED APPLICATIONS

This application is a continuation of U.S. application Ser. No. 11/461,045, filed Jul. 31, 2006, which claims benefit of U.S. provisional application Ser. No. 60/747,166 filed May 12, 2006, and entitled "Percutaneous Tissue Excision Devices and Methods," and U.S. provisional application Ser. No. 60/704,224 filed Jul. 29, 2005, and entitled "Device for Resecting Spinal Tissue," all of which are incorporated herein by reference in their entirety and to which applications we claim priority under 35 USC §120.

STATEMENT REGARDING FEDERALLY SPONSORED RESEARCH OR DEVELOPMENT

Not Applicable

BACKGROUND

1. Field of the Invention

The present invention relates generally to minimally invasive methods, devices and systems for treating spinal disorders using imaging guidance. More particularly, the present invention relates to devices and methods to reduce stenosis and increase the cross-sectional area of the spinal canal available for the spinal cord. Still more particularly, the present invention relates to devices and methods to percutaneously excise portions of an enlarged ligamentum flavum.

2. Background of the Invention

The vertebral column (spine, spinal column, backbone) forms the main part of the axial skeleton, provides a strong yet flexible support for the head and body, and protects the spinal cord disposed in the vertebral canal, which is formed within the vertebral column. The vertebral column comprises a stack of vertebrae with an intervertebral disc between adjacent vertebrae. The vertebrae are stabilized by muscles and ligaments that hold the vertebrae in place and limit the movements of the vertebrae.

As illustrated in FIG. 1, each vertebra 10 includes a vertebral body 12 that supports a vertebral arch 14. A median plane 210 generally divides vertebra 10 into two substantially equal lateral sides. Vertical body 12 has the general shape of a short cylinder and is anterior to the vertebral arch 14. The vertebral arch 14 together with vertebral body 12 encloses a space termed the vertebral foramen 15. The succession of vertebral foramen 15 in adjacent vertebrae 10 along the vertebral column define the vertebral canal (spinal canal), which contains the spinal cord.

Vertebral arch 14 is formed by two pedicles 24 which project posteriorly to meet two laminae 16. The two laminae 16 meet posteriomedially to form the spinous process 18. At the junction of pedicles 24 and laminae 16, six processes arise. Two transverse processes 20 project posterolaterally, two superior articular processes 22 project generally superiorly and are positioned superior to two inferior articular processes 25 that generally project inferiorly.

The vertebral foramen 15 is generally an oval shaped space that contains and protects the spinal cord 28. Spinal cord 28 comprises a plurality of nerves 34 surrounded by cerebrospinal fluid (CSF) and an outermost sheath/membrane called the dural sac 32. The CSF filled dural sac 32 containing nerves 34 is relatively compressible. Posterior to the spinal cord 28 within vertebral foramen 15 is the ligamentum flavum 26

Laminae 16 of adjacent vertebral arches 14 in the vertebral column are joined by the relatively broad, elastic ligamentum flavum 26.

In degenerative conditions of the spine, narrowing of the spinal canal (stenosis) can occur. Lumbar spinal stenosis is often defined as a dural sac cross-sectional area less than 100 mm$^2$ or an anterior-posterior (AP) dimension of the canal of less than 10-12 mm for an average male.

The source of many cases of lumbar spinal stenosis is thickening of the ligamentum flavum. Spinal stenosis may also be caused by subluxation, facet joint hypertrophy, osteophyte formation, underdevelopment of spinal canal, spondylosis deformans, degenerative intervertebral discs, degenerative spondylolisthesis, degenerative arthritis, ossification of the vertebral accessory ligaments and the like. A less common cause of spinal stenosis, which usually affects patients with morbid obesity or patients on oral corticosteroids, is excess fat in the epidural space. The excessive epidural fat compresses the dural sac, nerve roots and blood vessels contained therein and resulting in back, leg pain and weakness and numbness of the legs. Spinal stenosis may also affect the cervical and, less commonly, the thoracic spine.

Patients suffering from spinal stenosis are typically first treated with exercise therapy, analgesics, and anti-inflammatory medications. These conservative treatment options frequently fail. If symptoms are severe, surgery is required to decompress the spinal cord and nerve roots.

In some conventional approaches to correct stenosis in the lumbar region, an incision is made in the back and the muscles and supporting structures are stripped away from the spine, exposing the posterior aspect of the vertebral column. The thickened ligamentum flavum is then exposed by removal of a portion of the vertebral arch, often at the laminae, covering the back of the spinal canal (laminectomy). The thickened ligamentum flavum ligament can then be excised by sharp dissection with a scalpel or punching instruments such as a Kerison punch that is used to remove small chips of tissue. The procedure is performed under general anesthesia. Patients are usually admitted to the hospital for approximately five to seven days depending on the age and overall condition of the patient. Patients usually require between six weeks and three months to recover from the procedure. Further, many patients need extended therapy at a rehabilitation facility to regain enough mobility to live independently.

Much of the pain and disability after an open laminectomy results from the tearing and cutting of the back muscles, blood vessels, supporting ligaments, and nerves that occurs during the exposure of the spinal column. Also, because the spine stabilizing back muscles and ligaments are stripped and detached from the spine during the laminectomy, these patients frequently develop spinal instability post-operatively.

Minimally invasive techniques offer the potential for less post-operative pain and faster recovery compared to traditional open surgery. Percutaneous interventional spinal procedures can be performed with local anesthesia, thereby sparing the patient the risks and recovery time required with general anesthesia. In addition, there is less damage to the paraspinal muscles and ligaments with minimally invasive techniques, thereby reducing pain and preserving these important stabilizing structures.

Various techniques for minimally invasive treatment of the spine are known. Microdiscectomy is performed by making a small incision in the skin and deep tissues to create a portal to the spine. A microscope is then used to aid in the dissection of the adjacent structures prior to disceetomy. The recovery for this procedure is much shorter than traditional open discectomies. Percutaneous discectomy devices with fluoroscopic guidance have been used successfully to treat disorders of the disc but not to treat spinal stenosis or the ligamentum flavum directly. Arthroscopy or direct visualization of the spinal structures using a catheter or optical system have also been proposed to treat disorders of the spine including spinal stenosis, however these devices still use miniaturized standard surgical instruments and direct visualization of the spine similar to open surgical procedures. These devices and techniques are limited by the small size of the canal and these operations are difficult to perform and master. In addition, these procedures are painful and often require general anesthesia. Further, the arthroscopy procedures are time consuming and the fiber optic systems are expensive to purchase and maintain.

Still further, because the nerves of the spinal cord pass through the spinal canal directly adjacent to and anterior to the ligamentum flavum, any surgery, regardless of whether open or percutaneous, includes a risk of damage to the nerves of the spinal cord.

Hence, it remains desirable to provide simple methods, techniques, and devices for treating spinal stenosis and other spinal disorders without requiring open surgery. It is further desired to provide a system whereby the risk of damage to the dural sac containing the spinal nerves may be reduced.

BRIEF SUMMARY OF SOME OF THE PREFERRED EMBODIMENTS

These and other needs in the art are addressed in one embodiment by a device for percutaneously excising tissue. In an embodiment, the device comprises an outer tubular member. In addition, the device comprises an inner tubular member slidingly received within the outer tubular member, wherein the inner tubular member has a distal end including an upper member and a lower member. Further, the device includes an open position with the distal end fully extended from the outer tubular, and a closed position with the distal end disposed within the outer tubular, wherein the upper member is biased away from the lower member and is disposed at an open angle $\theta_O$ relative to the lower member when the device is in the opened position.

These and other needs in the art are addressed in another embodiment by a method for treating stenosis in a spine of a patient having a median plane, the spine including a spinal canal having a posterior surface, a dural sac and an epidural space between the posterior surface and dural sac, the location of the stenosis determining a region of interest in the spine. In an embodiment, the method comprises the step of positioning a tissue excision device adjacent the region of interest, wherein the tissue excision device comprises an outer tubular member and an inner tubular member slidably received within the outer tubular member, wherein the inner tubular member has a distal end including an upper member and a lower member. In addition, the method comprises the step of opening the tissue excision device by extending the distal end of the inner tubular from the outer tubular. Further, the method comprises the step of inserting the tissue excision device into tissue in the region of interest. Still further, the method comprises the step of closing the tissue excision device by sliding the outer tubular over the distal end of the inner tubular. Moreover, the method comprises the step of retracting the tissue excision device from the tissue in the region of interest.

These and other needs in the art are addressed in another embodiment by a kit for performing a procedure on a spine, the spine including an epidural space containing a dural sac. In an embodiment, the kit comprises an insertion member for accessing the epidural space. In addition, the kit comprises a volume of a contrast medium adapted to be inserted into the epidural space by the insertion member and expanded so as to compress a portion of the thecal sac and provide a safety zone within the epidural space. Further, the kit comprises a tissue excision device comprising an outer tubular member and an inner tubular member slidably received within the outer tubular member, wherein the inner tubular member has a distal end including an upper member and a lower member.

Thus, embodiments described herein comprise a combination of features and advantages intended to address various shortcomings associated with certain prior devices. The various characteristics described above, as well as other features, will be readily apparent to those skilled in the art upon reading the following detailed description of the preferred embodiments, and by referring to the accompanying drawings. It should be appreciated by those skilled in the art that the conception and the specific embodiments disclosed may be readily utilized as a basis for modifying or designing other structures for carrying out the same purposes of the embodiments described herein. It should also be realized by those skilled in the art that such equivalent constructions do not depart from the spirit and scope of the invention as set forth in the appended claims.

BRIEF DESCRIPTION OF THE DRAWINGS

For a more complete understanding of the invention, reference is made to the accompanying drawings, wherein:

FIG. 3 is an enlarged cross-section of a vertebral foramen, showing a safety zone created by compression of the dural sac;

FIG. 4 is the cross-section of FIG. 3, showing a tissue excision tool positioned in the ligamentum flavum according to a first method (ILAMP);

FIG. 5 is the cross-section of FIG. 3, showing a tissue excision tool positioned in the ligamentum flavum according to an alternative method (MILD);

DETAILED DESCRIPTION OF THE PREFERRED EMBODIMENTS

Figure 1:
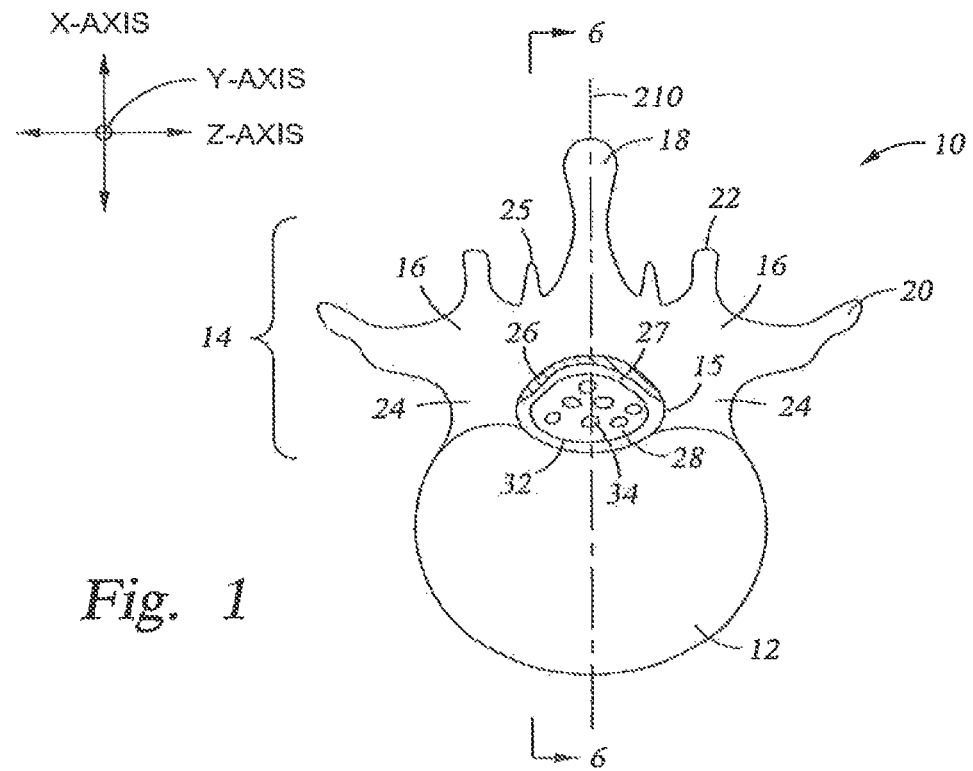
FIG. 1 is cross-section of the spine viewed from the space between two vertebrae, showing the upper surface of one vertebra and the spinal canal with the dural sac and a normal (un-stenosed) ligamentum flavum therein.

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

For purposes of this discussion, the x-, y-, and z-axes are shown in FIGS. 1, 3, 5, 6, and 7 to aid in understanding the descriptions that follow. The x-, y-, and z-axes have been assigned as follows. The x-axis is perpendicular to the longitudinal axis of the vertebral column and perpendicular to the coronal/frontal plane (i.e., x-axis defines anterior vs. posterior relationships). The y-axis runs substantially parallel to the vertebral column and perpendicular to the transverse plane (i.e., y-axis defines superior vs. inferior relationships). The z-axis is perpendicular to the longitudinal axis of the vertebral column and perpendicular to the median/midsagittal plane (i.e., z-axis defines the lateral right and left sides of body parts). The set of coordinate axes (x-, y-, and z-axes) are consistently maintained throughout although different views of vertebrae and the spinal column may be presented.

It is to be understood that the median/midsagittal plane passes from the top to the bottom of the body and separates the left and the right sides of the body, and the spine, into substantially equal halves (e.g., two substantially equal lateral sides). Further, it is to be understood that the frontal/coronal plane essentially separates the body into the forward (anterior) half and the back (posterior) half, and is perpendicular to the median plane. Still further, it is to be understood that the transverse plane is perpendicular to both the median plane and coronal plane and is the plane which divides the body into an upper and a lower half.

The Spinal Canal and Spinal Stenosis

Referring again to FIG. 1, vertebral foramen 15 contains a portion of the ligamentum flavum 26, spinal cord 28, and an epidural space 27 between ligamentum flavum 26 and spinal cord 28. Spinal cord 28 comprises a plurality of nerves 34 surrounded by cerebrospinal fluid (CSF) contained within dural sac 32. Nerves 34 normally comprise only a small proportion of the dural sac 32 volume. Thus, CSF filled dural sac 32 is somewhat locally compressible, as localized pressure causes the CSF to flow to adjacent portions of the dural sac. Epidural space 27 is typically filled with blood vessels and fat. The posterior border of the normal epidural space 27 generally defined by the ligamentum flavum 26, which is shown in its normal, non-thickened state in FIG. 1.

Figure 2:
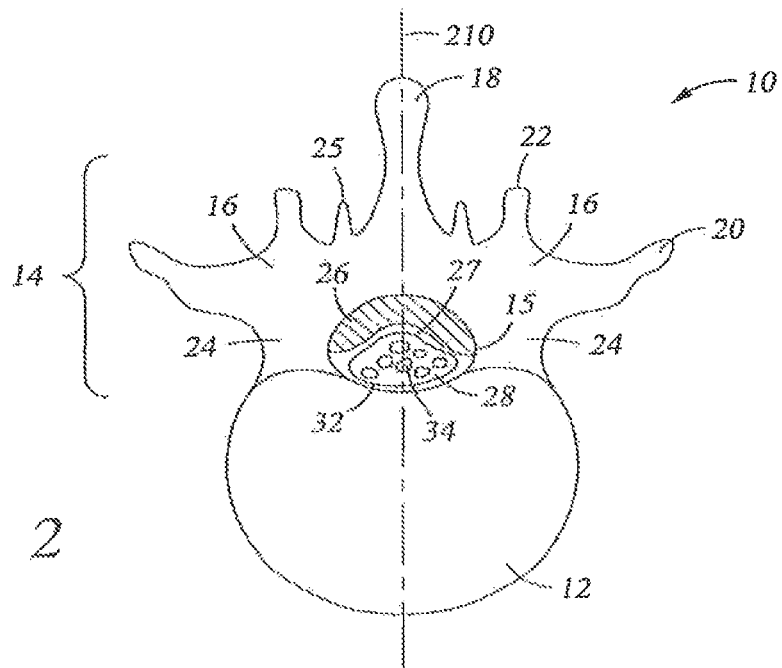
FIG. 2 is an illustration of the same section as FIG. 1, showing the spinal canal with the dural sac and a thickened ligamentum flavum therein.

FIG. 2 illustrates a case of spinal stenosis resulting from a thickened ligamentum flavum 26 Since vertebral foramen 15 is defined and surrounded by the relatively rigid bone its volume is essentially constant Thus, thickening of ligamentum flavum 26 within vertebral foramen 15 can eventually result in compression of spinal cord 28. In particular, the thickened ligamentum flavum 26 may exert a compressive force on the posterior surface of dural sleeve 32. In addition, thickening of ligamentum flavum 26 may compress the blood vessels and fat occupying epidural space 27.

Compression of spinal cord 28, particularly in the lumbar region, may result in low back pain as well as pain or abnormal sensations in the legs. Further, compression of the blood vessels in the epidural space 27 that houses the nerves of the cauda equina may result in ischemic pain termed spinal claudication.

In order to relieve the symptoms associated with a thickened or enlarged ligamentum flavum 26, methods, techniques, and devices described herein may be employed to reduce the compressive forces exerted by the thickened ligamentum flavum on spinal cord 28 and the blood vessels in epidural space 27 (e.g., decompress spinal cord 28 and blood vessels in epidural space 27). In particular, compressive forces exerted by the thickened/enlarged ligamentum flavum 26 may be reduced by embodiments of a minimally invasive ligament decompression (MILD) procedure described herein. In some embodiments, the MILD procedure may be performed percutaneously to reduce the size of ligamentum flavum 26 by excising portions of ligamentum flavum 2. In particular, in some embodiments of the MILD procedure, the ligamentum flavum 26 is accessed, cut and removed ipsilaterally (i.e., on the same side of vertebral arch 14) by a percutaneous cranial-caudal approach. Such an embodiment of the MILD procedure may be described hereinafter as Ipsilateral Approach MILD Procedure (ILAMP).

Creation of a Safety Zone

As shown in FIGS. 1 and 2, ligamentum flavum 26 is posteriorly apposed to spinal cord 28. Thus, placement of tools within ligamentum flavum 26 to excise portions of ligamentum flavum 26 creates a risk of for inadvertent damage to the spinal cord 28, dural sac 32, and/or nerves 34. Thus, in preferred embodiments of the procedures described herein, prior to insertion of tissue excision devices into the ligamentum flavum 26, a gap is advantageously created between ligamentum flavum 26 and spinal cord 28 to provide a safety zone between ligamentum flavum 26 and spinal cord 28.

FIG. 3 illustrates an enlarged cross-sectional view of a vertebral foramen 15 within a vertebra. Vertebral foramen 15 includes epidural space 27 and spinal cord 28 containing nerves 34 and CSF within dural sac 32. Further, a thickened/enlarged ligamentum flavum 26 extends into vertebral foramen 15. To reduce the risk of damage to dural sac 32 and spinal cord 28, a safety zone 40 is created between ligamentum flavum 26 and dural sac 32.

As previously described, spinal cord 28 comprises nerves 34 surrounded by CSF and is contained within dural sac 32. Since more than 90% of the volume of dural sac 32 in the lumbar region is filled by CSF, dural sac 32 is highly compressible. Thus, even when stenosis is causing compression of spinal cord 28, in most cases it is possible to temporarily compress spinal cord 28 further. Thus, according to preferred embodiments, dural sac 32 is further compressed in the region of interest by injecting a fluid into epidural space 27 to create safety zone 40. The fluid may be injected into the epidural space 27 with an insertion member, such as a needle. The presence of the injected fluid comprising safety zone 40 gently applies an additional compressive force to the outer surface of dural sac 32 so that at least a portion of the CSF within dural sac 32 is forced out of dural sac 32 in the region of interest, resulting in safety zone 40 between dural sac 32 and ligamentum flavum 26.

According to some embodiments, dural sac 32 is compressed by injecting a standard radio-opaque non-ionic myelographic contrast medium or other imagable or non-imagable medium into epidural space 27 in the region of interest. This is preferably accomplished with a percutaneous injection. Sufficient injectable fluid is preferably injected to displace the CSF out of the region of interest and compress dural sac 32 to at least a desired degree. The injected medium is preferably substantially contained within the confines of epidural space 27 extending to the margins of the dural sac 32. The epidural space is substantially watertight and the fatty tissues and vascularization in epidural space 27, combined with the viscous properties of the preferred fluids, serve to substantially maintain the injected medium in the desired region of interest. This novel method for protecting spinal cord 28 column may be referred to hereinafter as "contrast-guided dural protection."

Once a safety zone 40 has been created, a tissue excision tool or device 100 may be inserted into the ligamentum flavum 26. Device 100 may comprise any suitable device, tool or instrument for relieving stenosis caused by the thickened/enlarged ligamentum flavum 26 including without limitation, embodiments of tissue excision devices and tissue retraction devices described in more detail below. Further, as best illustrated in FIG. 4, device 100 is inserted and positioned in the ligamentum flavum 26 on the same side (ipsilateral) of median plane 210 as device 100 percutaneously accesses the body, such that device 100 does not cross median plane 210. In another embodiment, as best illustrated in FIG. 4, device 100 is positioned in the ligamentum flavum 26 on the opposite side of median plane 210 as device 100 percutaneously accesses the body, such that device 100 crosses median plane 210. In some embodiments, tissue excision device 100 may be guided by and advanced through a cannula toward the ligamentum flavum 26. In other embodiments, a cannula is not be employed to guide device 100 as it is advanced toward ligamentum flavum 26.

While it is preferred that the tip of device 100 remain within ligamentum flavum 26 as shown, the presence of safety zone 40 reduces the likelihood that dural sac 32 will be damaged, even if the tip of device 100 breaks through the anterior surface of ligamentum flavum 26.

Because the present techniques are preferably performed percutaneously, certain aspects of the present invention may be facilitated by imaging. Imaging windows (e.g., a fluoroscopic window of access—FWA) may be employed to aid in performance of all or part of the procedures described herein. For instance, an imaging window may be employed to aid in insertion of device 100 into ligamentum flavum 26 as shown in FIG. 4. Preferable imaging windows/views are described in more detail below.

In this context, the spine can be imaged using any suitable technology, including without limitation, 2D fluoroscopy, 3D fluoroscopy, CT, MRI, ultrasound or with direct visualization with fiber optic or microsurgical techniques. Stereotactic or computerized image fusion techniques are also suitable. Fluoroscopy is currently particularly well-suited to the techniques disclosed herein. Fluoroscopic equipment is safe and easy to use, readily available in most medical facilities, relatively inexpensive. In a typical procedure, using direct biplane fluoroscopic guidance and local anesthesia, epidural space 27 is accessed for injection of contrast media adjacent to the surgical site.

If the injected medium is radio-opaque, as are for example myelographic contrast media, the margins of expanded epidural space 27 will be readily visible using fluoroscopy or CT imaging. Thus, safety zone 40 created by the present contrast-guided dural compression techniques can reduce the risk of damage to dural sac 32 and spinal cord 28 during MILD procedures to remove or displace portions of ligamentum flavum 26 and/or laminae 16 in order to treat spinal stenosis.
Injectable Medium If desired, the injected medium can be provided as a re-absorbable water-soluble gel, so as to better localize safety zone 40 at the site of surgery and reduce leakage of this protective layer from the vertebral/spinal canal. An injectable gel is a significant improvement on prior epidural injection techniques. The gel is preferably substantially more viscid than conventional contrast media and the relatively viscid and/or viscous gel preferably tends to remain localized at the desired site of treatment as it does not spread as much as standard liquid contrast media that are used in epidurography. This may result in more uniform compression of dural sac 32 and less leakage of contrast out of the vertebral/spinal canal. In addition, preferred embodiments of the gel are re-absorbed more slowly than conventional contrast media, allowing for better visualization during the course of the surgical procedure.

In some embodiments, a contrast agent can be included in the gel itself, so that the entire gel mass is imagable. In other embodiments, an amount of contrast can be injected first, followed by the desired amount of gel, or an amount of gel can be injected first, followed by the desired amount of contrast. In this case, the contrast agent is captured on the surface of the expanding gel mass, so that the periphery of the mass is imagable.

Any standard hydrophilic-lipophilic block copolymer (Pluronic) gel such as are known in the art would be suitable and other gels may be used as the injectable medium. The gel preferably has an inert base. In certain embodiments, the gel material is liquid at ambient temperatures and can be injected through a small bore, such as a 27 gauge needle. The gel then preferably becomes viscous when warmed to body temperature after being injected. The viscosity of the gel can be adjusted through the specifics of the preparation. The gel or other fluid is preferably sufficiently viscid or viscous at body temperature to compress and protect dural sac 32 in the manner described above and to remain sufficiently present in the region of interest for at least about 30 minutes. Thus, in some embodiments, the injected gel attains a viscosity that is two, three, six or even ten times that of the fluids that are typically used for epidurograms.

In certain embodiments, the injected medium undergoes a reversible change in viscosity when warmed to body temperature so that it can be injected as a low-viscosity fluid, thicken upon injection into the patient, and be returned to its low-viscosity state by cooling. In these embodiments, the injected medium is injected as desired and thickens upon warming, but can be removed by contacting it with a heat removal device, such as an aspirator that has been provided with a cooled tip. As a result of localized cooling, the gel reverts to its initial non viscous liquid state and can be easily suctioned up the cooled needle or catheter.

An example of a suitable contrast medium having the desired properties is Omnipaque® 240 available from Nycomed, N.Y., which is a commercially available non-ionic iodinated myelographic contrast medium. Other suitable injectable media will be known to those skilled in the art. Because of the proximity to spinal cord 28 and spinal nerves 34, it is preferred not to use ionic media in the injectable medium. The preferred compositions are reabsorbed relatively rapidly after the procedure. Thus any residual gel compression on dural sac 32 after the MILD procedure dissipates relatively quickly. For example, in preferred embodiments, the gel would have sufficient viscosity to compress dural sac 32 for thirty minutes, and sufficient degradability to be substantially reabsorbed within approximately two hours.

The injected contrast medium further may further include one or more bioactive agents. For example, medications such as those used in epidural steroid injection (e.g. Depo medrol, Celestone Soluspan) may be added to the epidural gel to speed healing and reduce inflammation, scarring and adhesions. The gel preferably releases the steroid medication slowly and prolongs the anti-inflammatory effect, which can be extremely advantageous. Local anesthetic agents may also be added to the gel. This prolongs the duration of action of local anesthetic agents in the epidural space to prolong pain relief during epidural anesthesia. In this embodiment the gel may be formulated to slow the reabsorption of the gel.

The present gels may also be used for epidural steroid injection and perineural blocks for management of acute and chronic spinal pain. Thrombin or other haemostatic agents can be added if desired, so as to reduce the risk of bleeding.

In some embodiments, the gel may also be used as a substitute for a blood patch if a CSF leak occurs. The gel may also be used as an alternative method to treat lumbar puncture complications such as post-lumbar puncture CSF leak or other causes of intracranial hypotension. Similarly, the gel may be used to patch postoperative CSF leaks or dural tears. If the dural sac were inadvertently torn or cut, then gel could immediately serve to seal the site and prevent leakage of the cerebral spinal fluid.

Ipsilateral Approach for MILD Procedure (ILAMP)

Once safety zone 40 has been created, the margins of epidural space 27 are clearly demarcated by the injected medium and may be visualized radiographically if an imageable medium has been used. As mentioned above, percutaneous procedures can then more safely be performed on ligamentum flavum 26 and/or surrounding tissues with reduced potential for injuring dural sac 32 and spinal cord 28.

A variety of suitable techniques and devices may be employed to reduce the size of the thickened/enlarged ligamentum flavum 26, thereby decompressing spinal cord 28 as well as blood vessels contained within the epidural space 27. Examples of suitable decompression techniques include without limitation, removal of tissue from ligamentum flavum 26, laminectomy, laminotomy, and retraction and anchoring of ligamentum flavum 26. In some embodiments, all or a portion of ligamentum flavum 26 is excised using a tissue excision device or tool (e.g., device 100). Embodiments of tissue excision tools are described in more detail below.

Accessing ligamentum flavum 26 with a tissue excision device 100 to remove portions of ligamentum flavum 26 can present significant challenges. For instance, in some conventional approaches to correct stenosis caused by an enlarged ligamentum flavum, an incision is made in the back of the patient and then the muscles and supporting structures of the vertebral column (spine) are stripped away, exposing the posterior aspect of the vertebral column. Subsequently, the thickened ligamentum flavum is exposed by removal of a portion of vertebral arch 14, often at lamina 16, which encloses the anterior portion of the spinal canal (laminectomy). The thickened ligamentum flavum ligament can then be excised by sharp dissection with a scalpel or punching instruments. However, this approach is usually performed under general anesthesia and typically requires an extended hospital stay, lengthy recovery time and significant rehabilitation. Referring briefly to FIG. 2, as another example, some MILD procedures access ligamentum flavum 26 percutaneously by boring a hole through the vertebral arch 14 of vertebra 10, often through a lamina 16. A cannula and/or device 100 may be passed through the bore and/or anchored to the bore to access ligamentum flavum 26 for excision. However, while such a MILD approach is minimally invasive and reduces recovery time, such an approach requires the additional step of boring a hole in the posterior of the vertebra 10 of interest. Thus, in some cases it will be preferable to employ a MILD that percutaneously accesses ligamentum flavum 26 without the need to cut or bore through the vertebrae.

Figure 6:
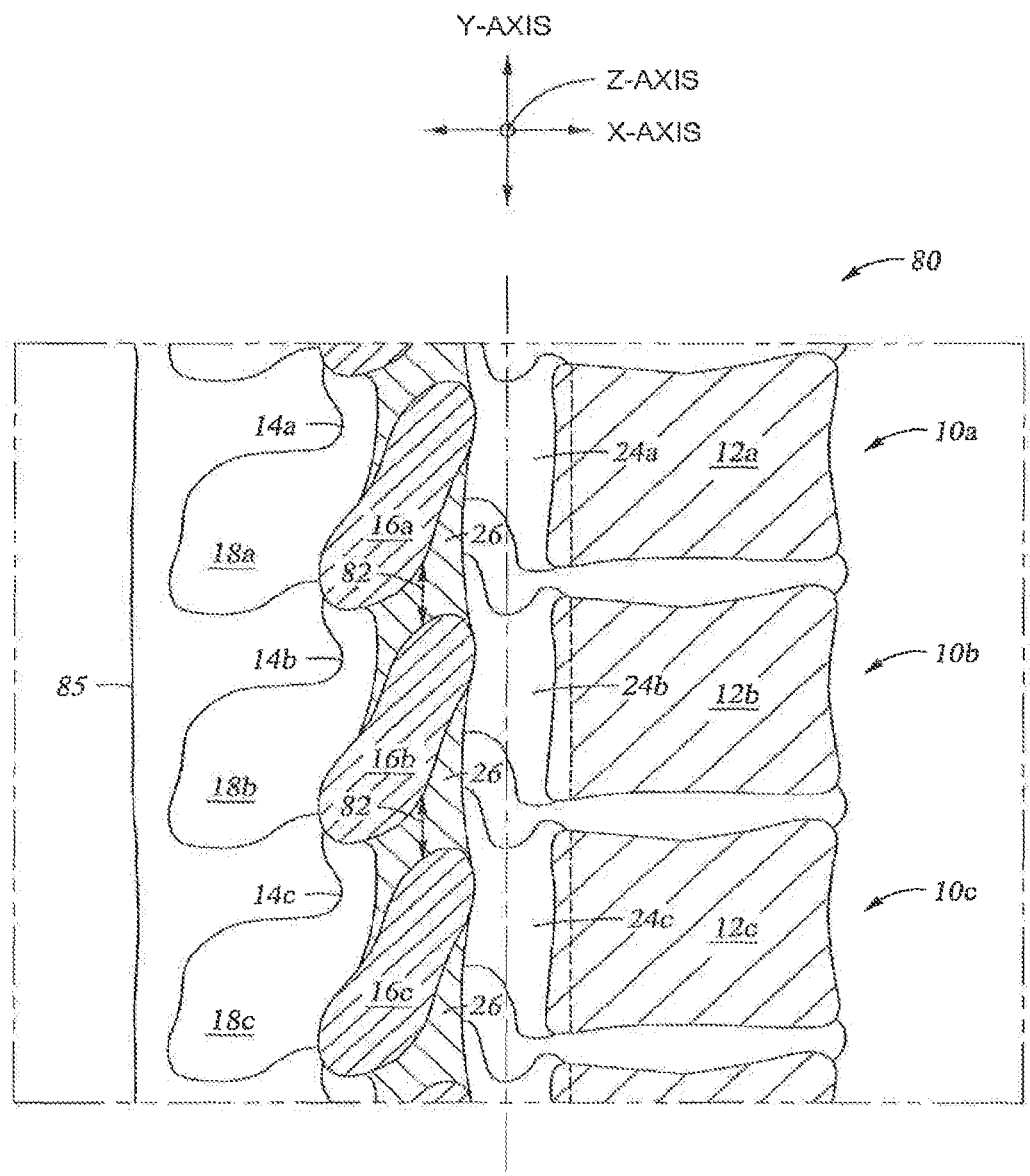
FIG. 6 is a partial cross-section of the lumbar portion of the vertebral column taken along lines 6-6 in FIG. 1.

FIG. 6 is a partial cross-sectional lateral view of a segment of a vertebral column 80. The segment of vertebral column 80 illustrated in FIG. 5 includes three vertebrae 10a, 10b, and 10c. Each vertebra 10a, 10b, 10c includes a vertebral body 12a, 12b, 12c, that supports a vertebral arch 14a, 14b, 14c, respectively Vertical body 12a, 12b, 12c is anterior to vertebral arch 14a, 14b, 14c, respectively. Each vertebral arch 14a, 14b, 14c together with vertebral body 12a, 12b, 12c, respectively, encloses a vertebral foramen 15a, 15b, 15c. The succession of vertebral foramen 15a, 15b, 15c in adjacent vertebrae 10a, 10b, 10c define vertebral canal 81 (spinal canal) that runs along the length of vertebral column 80. Vertebral canal 81 contains the spinal cord (not shown in FIG. 5).

As previously described, each vertebral arch 14a, 14b, 14c includes two pedicles 24a, 24b, 24c, which project posteriorly to meet two lamina 16a, 16b, 16c, respectively. It is to be understood that in this view, one pedicle has been removed from each vertebra 10a, 10b, 10c and only the cross-section of one lamina 16a, 16b, 16c is visible. The two lamina 16a, 16b, 16c meet posteriomedially to form the spinous process 18a, 18b, 18c, respectively.

Lamina 16a, 16b, 16c of adjacent vertebra 10a, 10b, 10c are connected by ligamentum flavum 26 (shown in cross-section). The relatively elastic ligamentum flavum 26 extends almost vertically from superior lamina to inferior lamina of adjacent vertebrae. In particular, ligamentum flavum 26 originates on the inferior surface of the laminae of the superior vertebrae and connects to the superior surface of the laminae of the inferior vertebrae. For instance, ligamentum flavum 26 originates on the inferior surface of lamina 16a of superior vertebra 10a and connects to the superior surface of lamina 16b of the inferior vertebra 10b. Thus, ligamentum flavum 26 spans an interlaminar space 82 (i.e., space between laminae of adjacent vertebrae). Interlaminar space 82 is generally the space between laminae of adjacent vertebrae in spinal column 80.

Still referring to FIG. 6, each lamina 16a, 16b, 16c comprises a relatively broad flat plate of bone that extends posteromedially and slightly inferiorly from pedicles 24a, 24b, 24c, respectively. Along the length of vertebral column 80, the lamina 16a, 16b, 16c overlap like roofing shingles, with each lamina substantially parallel to and at least partially overlapping the adjacent inferior lamina. Further, the adjacent substantially parallel laminae are separated by the intervening ligamentum flavum 26 and interlaminar space 82. For instance, lamina 16a is substantially parallel to and partially overlaps adjacent inferior lamina 16b and is separated from lamina 16b by ligamentum flavum 26 and interlaminar space 82.

Figure 7:
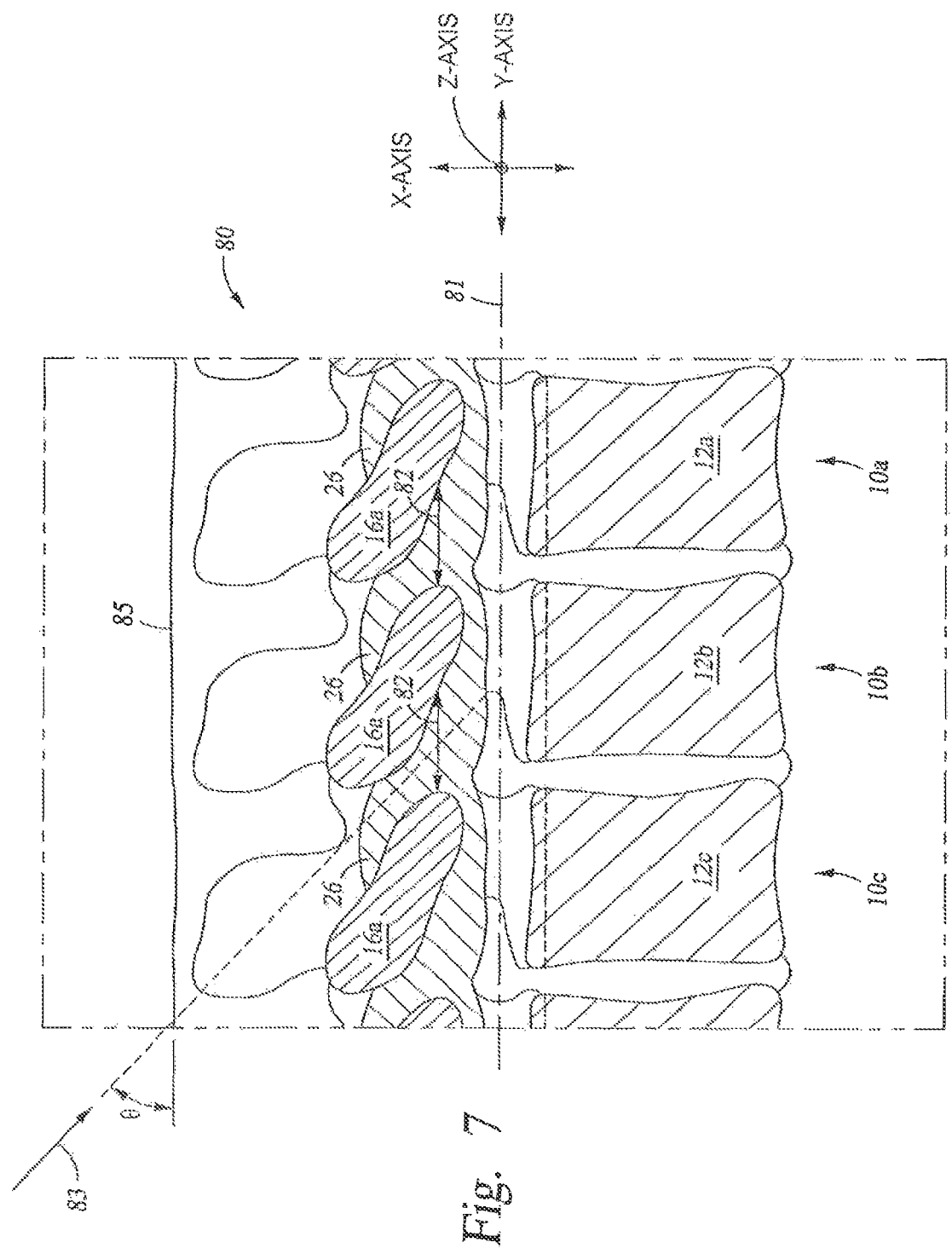
FIG. 7 is the cross-section of FIG. 6, showing the orientation of an imaging tool relative to the vertebral column.

FIG. 7 illustrates vertebral column 80 as it may be oriented with the anterior side positioned down and posterior back surface 85 positioned upward, as may be encountered during a spinal procedure or surgery. In addition, in the embodiment illustrated in FIG. 6, ligamentum flavum 26 is thickened/enlarged, resulting in spinal stenosis. In particular, the anterior portions of enlarged ligamentum flavum 26 are extending into spinal canal 81, potentially exerting compressive forces on the spinal cord (not shown) that resides within spinal canal 81.

As previously discussed, to relieve compressive forces on the spinal cord and hence relieve the associated symptoms of spinal stenosis, portions of ligamentum flavum 26 may be excised. However, to percutaneously excise portions of ligamentum flavum 26 via minimally invasive techniques, the innate structure of vertebral column 80 and each vertebra may present significant imaging challenges. For instance, lateral imaging windows/views of ligamentum flavum 26 substantially in the direction of the z-axis may be obscured by the various processes of the vertebrae (e.g., transverse processes, superior articular processes, inferior articular processes), the laminae of each vertebra, etc. Further, some anterior-posterior (A-P) imaging windows/views of ligamentum flavum 26 substantially in the direction of the x-axis may also be obscured by the laminae. In particular, in the A-P radiographic imaging planes substantially in the direction of the x-axis, the posterior edges of parallel laminae overlap and obscure ligamentum flavum 26 and interlaminar space 82, particularly the anterior portions of ligamentum flavum 26 and interlaminar space 82 closest to spinal canal 81. However, with an imaging window/view in a plane substantially parallel to the X-Y plane, at an angle θ generally in the direction of arrow 83, and slightly lateral to the spinous process, interlaminar space 82 and ligamentum flavum 26 may be viewed without significant obstruction from neighboring laminae. In other words, imaging windows/views generally aligned with arrow 83 (FIG. 6) allow a more direct view of interlaminar space 82 and ligamentum flavum 26 from the posterior back surface with minimal obstruction by the vertebrae, laminae in particular.

Typically, the long axes of the substantially parallel laminae (e.g., laminae 16a, 16b, 16c) and interlaminar spaces (e.g, interlaminar spaces 82) are generally oriented between 60 and 75 degrees relative to posterior back surface 85. Thus, preferably the imaging means (e.g., x-ray beam, fluoroscopy tube, etc.) is positioned generally in the direction represented by arrow 83, where θ is substantially between 60 and 75 degrees relative to the anterior back surface 85. In other words, the imaging means is positioned substantially parallel to the surface of the laminae. The resulting imaging window/view, termed "caudal-cranial posterior view" hereinafter, permits a clearer, more direct, less obstructed view of interlaminar space 82 and ligamentum flavum 26 from the general posterior back surface 85. The caudal-cranial posterior view permits a relatively clear view of interlaminar space 82 and ligamentum flavum 26 in directions generally along the y-axis and z-axis. However, the caudal-cranial posterior view by itself may not provide a clear imaging window/view of interlaminar space 82 and ligamentum flavum 26 in directions generally along the x-axis. In other words, the caudal-cranial posterior view by itself may not provide a clear imaging window/view that can be used to accurately determine the posterior-anterior depth, measured generally along the x-axis, of a device across the ligamentum flavum 26.

Thus, in preferred embodiments, an additional imaging window/view, termed "caudal-cranial posterior-lateral view" hereinafter, is employed to provide a clearer, unobstructed view of interlaminar space 82 and ligamentum flavum 26 in directions generally along the y-axis and z-axis. The caudal-cranial posterior-lateral view is generated by orienting an imaging means generally at an angle θ relative to outer surface of the patient and also angling such imaging means laterally in an oblique orientation, revealing a partial lateral view of interlaminar space 82 occupied by ligamentum flavum 26 on the anterior side of the lamina and posterior to the underlying dural sac (not shown) and spinal cord (not shown).

By employing at least one of the caudal-cranial posterior view and the caudal-cranial posterior-lateral views, relatively clear imaging windows/views of the interlaminar space 82 and ligamentum flavum 26 in directions along the x-, y-, and z-axes may be achieved.

Figure 8:
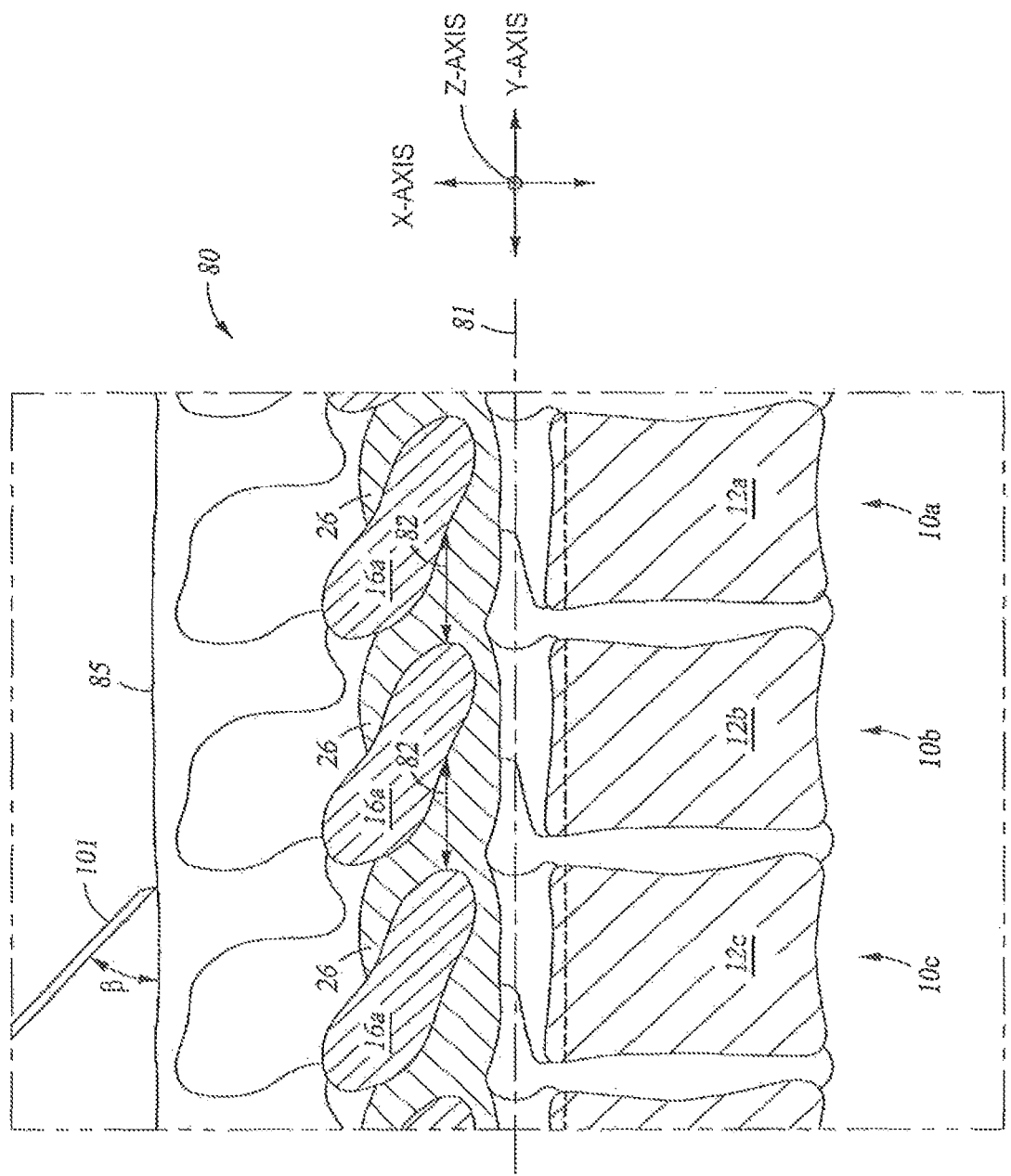
FIG. 8 is the cross-section of FIG. 6, showing the orientation of an instrument relative to the vertebral column.

FIG. 8 illustrates vertebral column 80 and an instrument 101. Once unobstructed imaging windows/views of interlaminar space 82 and ligamentum flavum 26 are established in the manner described above, instrument 101 is employed to percutaneously access interlaminar space 82 and ligamentum flavum 26. Instrument 101 may be any suitable device necessary to perform the MILD procedures described herein including without limitation a tissue excision device, a cannula employed to guide a tissue excision device, or combinations thereof. Tissue excision tools and devices are described in more detail below.

More specifically, using images of the interlaminar space 82 and ligamentum flavum 26 obtained from the desired direction(s), (e.g., caudal-cranial posterior view and the caudal-cranial posterior-lateral view), instrument 101 can be employed to penetrate the skin and soft tissue in the posterior back surface 85 of the patient. In preferred embodiments, the skin entry point for instrument 101 is between 5 and 10 cm inferior (caudal to) the posterior surface of the interlaminar space 82 of interest. For instance, if the portion of ligamentum flavum 26 between lamina 16a and lamina 16b is the area of interest, then instrument 101 may be inserted into the patient's back about 5 to 10 cm inferior to posterior surface 84 of interlaminar space 82.

Referring now to FIG. 7, instrument 101 is preferably initially inserted into the posterior tissue and musculature of the patient generally parallel to the longitudinal axis of spinal column 80. In other words, the angle β between the posterior back surface 85 and instrument 101 is between 0 and 10 degrees when instrument 101 is initially inserted. Further, instrument 101 is preferably inserted into the posterior tissue and musculature of the patient on the same side (ipsilateral) of the median plane as the area of interest (e.g., the targeted portion of ligamentum flavum 26), as best seen in FIG. 4. Once instrument 101 is inserted into the posterior tissue and musculature of the patient, instrument 101 then may be oriented 5 to 90 degrees relative to the posterior back surface 85 in order to create a trajectory across ligamentum flavum 26 in the area of interest. It is to be understood that once instrument 101 is inserted into the patients posterior back surface 85, the ends of instrument 101 are free to pivot about the insertion location in posterior back surface 85 in the general direction of the y-axis and the z-axis, and may be advanced posteriorly or anteriorly generally in the direction of the x-axis.

Once inserted into the posterior tissue and musculature of the patient, instrument 101 can be positioned to provide a trajectory across interlaminar space 82 in the area of interest, generally towards the anterior surface of the lamina superior to the area of interest. For example, if interlaminar space 82 between lamina 16a and lamina 16b is the area of interest, instrument 101 is positioned to provide a trajectory that will allow a cutting instrument to be inserted across interlaminar space 82 between lamina 16a and lamina 16b towards the anterior surface of lamina 16a (superior lamina).

By switching between the caudal-cranial posterior view and the caudal-cranial posterior-lateral view, or by viewing both the caudal-cranial posterior view and the caudal-cranial posterior-lateral view at the same time, instrument 101 can be advanced to ligamentum flavum 26 in the area of interest with more certainty than has heretofore been present. Once instrument 101 has reached ligamentum flavum 26, portions of ligament flavum 26 may be excised with a tissue excision device so as to relieve pressure on the spinal nerves. If instrument 101 comprises a tissue excision tool, instrument 101 may be inserted into ligamentum flavum 26 to resect portions of ligamentum flavum 26. However, if instrument 101 comprises a cannula, instrument 101 will be positioned adjacent the ligamentum flavum 26 in the region of interest and a tissue excision device may be advanced through instrument 101 toward ligamentum flavum 26 and inserted in ligament flavum 26 in the region of interest to retract tissue therefrom. In some embodiments, excision can be performed generally from posterior to anterior across interlaminar space 82 and then laterally along the anterior portion of ligament flavum 26 if desired. The actual depth of the tip of instrument 101 (or any tissue excision device passing through instrument 101 in the case instrument 101 is a cannula) in the general direction of the x-axis may be adjusted with guidance from the caudal-cranial posterior-lateral view and appropriate retraction/advancement of instrument 101 and appropriate adjustment of instrument 101 between 5 and 90 degrees relative to the posterior back surface 85.

Referring to FIG. 4, the tip of an exemplary tissue excision device 100 is shown schematically within ligamentum flavum 26. Tissue excision device 100 may be the same device as instrument 101, or may be a tool passed through instrument 101 if instrument 101 is a cannula. In particular, device 100 has accessed ligamentum flavum 26 according to the ILAMP method previously described. Thus, device 100 is positioned to excise portions of ligamentum flavum 26 on the same lateral side of median plane 210 as device 100 is percutaneously inserted. In other words, in the view shown in FIG. 4, device 100 is inserted into the body on the right side of median plane 210 and enters ligamentum flavum 26 on the right side of median plane 210 to excise portions of ligamentum flavum 26 on the right side of median plane 210. In FIG. 4, device 100 does not cross median plane 210.

FIG. 5 illustrates an embodiment of an alternative MILD method in which exemplary tissue excision device 100 is positioned to excise portions of ligamentum flavum 26 on the opposite lateral side of median plane 210 as device 100 is percutaneously inserted. More specifically, device 100 is inserted into the body on the rights side of median plane 210, enters ligamentum flavum 26 on the right side of median plane 210, but is positioned to excise portions of ligamentum flavum 26 on the left side of median plane 210. In FIG. 5, device 100 crosses median plane 210.

In the manner described, portions of the ligamentum flavum can be excised by a percutaneous MILD procedure. In particular, with the approach described and as best illustrated in FIGS. 4 and 6, ligamentum flavum 26 can be accessed, and portions thereof removed via the interlaminar space on the same lateral side (ipsilateral) of median plane 210 as the entry point for instrument 101 (e.g., a cannula, a tissue excision tool, etc.). This approach may sometimes hereinafter be referred to as an Iplsilateral Approach MILD Procedure (ILAMP).

Tissue Excision Devices

Embodiments of tissue excision tools, devices, and methods disclosed herein may take several forms and may be used according to the ILAMP method described above, or used according to alternative MILD procedures (e.g., MILD procedure schematically illustrated in FIG. 5). One such alternative MILD procedure is disclosed in U.S. application Ser. No. 11/193,581, which is hereby incorporated herein by reference in its entirety. In the descriptions of the tissue excision devices below, the distal portions of the devices are described in detail. As used herein, the term "distal" refers to positions that are relatively closer to the region of interest (e.g., the thickened portion of the ligamentum flavum to be decompressed). An exemplary embodiment of a proximal end for the tissue excision devices, including an actuation means, is also described below. However, it is to be understood that embodiments of tissue extraction devices described herein may be used with a variety of proximal ends and a variety of actuation means that are known and understood by those skilled in the art.

Figure 9:
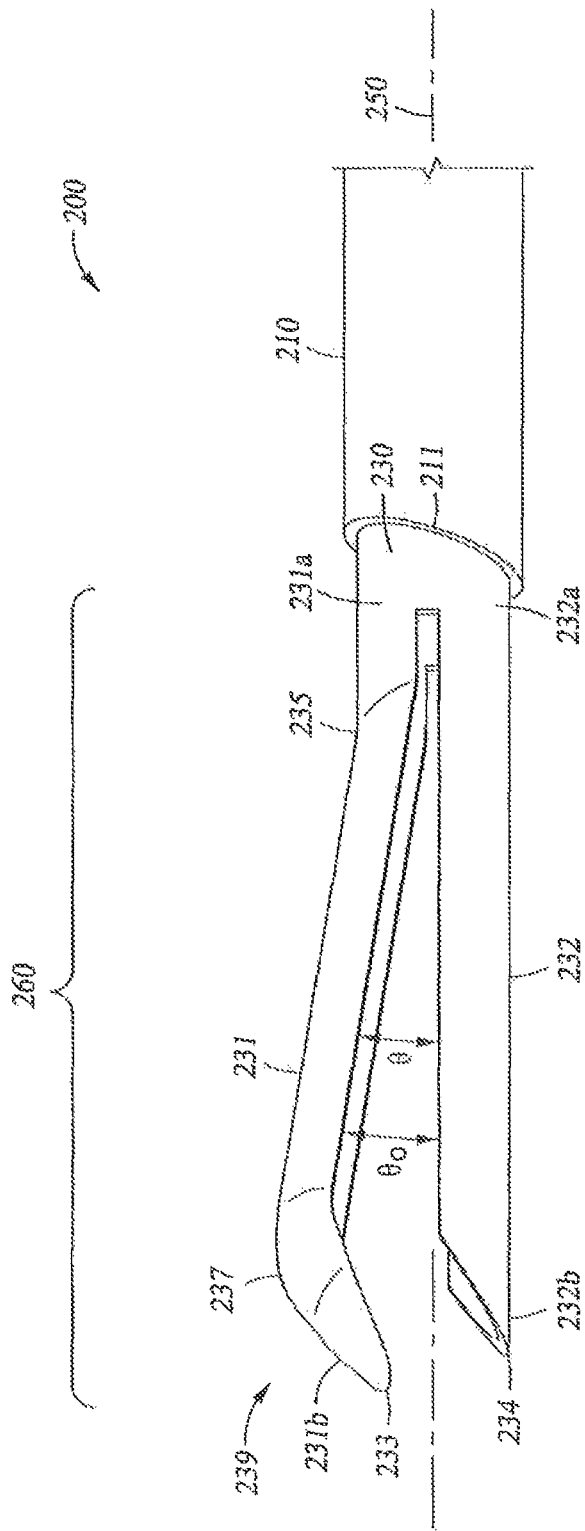
FIG. 9 is a perspective view of the distal portion of an embodiment of a tissue excision device in an open position
Figure 10:
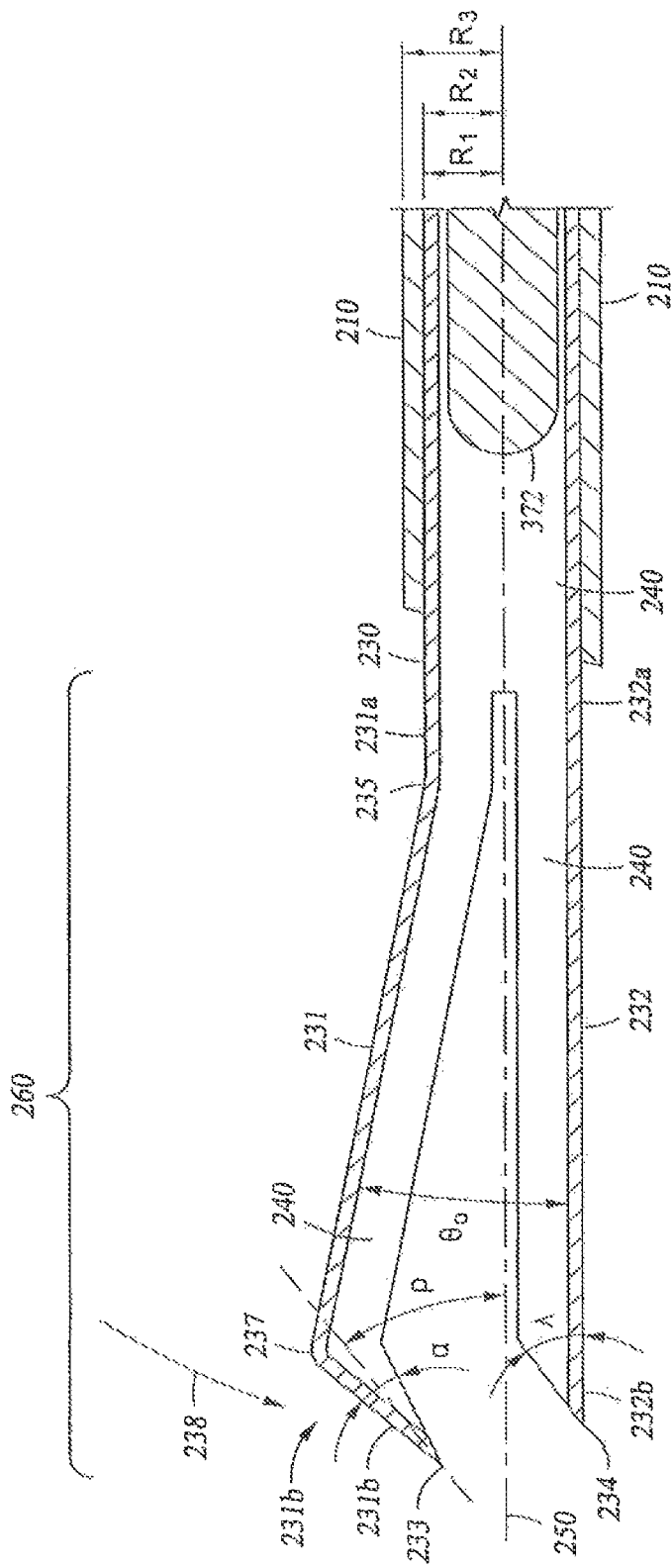
FIG. 10 is a cross-sectional view of the tissue excision device illustrated in FIG. 9.

FIGS. 9 and 10 illustrate the distal portion of an embodiment of a tissue excision device 200 in an opened position. Tissue excision device 200 comprises an inner tubular member 230 coaxially disposed within and slidingly engaging an outer tubular member 210. Inner and outer tubular members 230, 210 share a central longitudinal axis 250. Outer member 210 has an inner radius $R_1$, as measured from axis 250, and inner member 230 has an outer radius $R_2$, as measured from axis 250. In this embodiment, outer radius $R_2$ is substantially the same or slightly less than inner radius $R_1$ such that the outer surface of inner tubular 230 slidingly engages the inner surface of tubular 210. Thus, outer tubular 210 and inner tubular 230 are permitted to move axially (i.e., along axis 250) relative to each other. Tubulars 210, 230 may be formed from any suitable hollow bodies including without limitation a hypotube, cannula, or catheter. Although tubulars 210, 230 shown in FIGS. 9 and 10 generally have a circular cross-section, in general, members 210, 230 may have any suitable shape and cross-section including without limitation circular, oval, or rectangular.

Inner tubular 230 includes a central through bore 240 and a distal end 260. Bore 240 runs the length of inner tubular 230 and provides a void or space that may be filled with tissue excised by device 200 (e.g., excised pieces of ligamentum flavum). Distal end 260 includes an upper member 231 and a lower member 232. Distal end 260, including upper member 231 and lower member 232, completely extends from outer tubular 210 when device 200 is in the opened position as illustrated in FIGS. 9 and 10. Upper member 231 and lower member 232 are preferably integral with and formed from inner tubular 230. In such embodiments, distal end 260 of inner tubular 230 may be formed into an upper member 231 and lower member 232 by any suitable means including without limitation casting or molding, laser cuffing, machining, hot or cold working, or combinations thereof.

Lower member 232 preferably comprises a fixed end 232a integral with inner tubular 230 and a cutting end 232b, including a cutting tip 234, that cuts through tissue as lower member 232 is advanced through tissue. Cutting tip 234 preferably has a sharpened or beveled edge defined by an acute angle λ that is preferably between 15° and 45°. In the embodiment illustrated in FIGS. 9 and 10, lower member 232 is an extension of inner tubular 230 and thus is coaxial with outer tubular 210. As previously mentioned, lower member 232 is preferably integral with inner tubular 230. However, it should be understood that lower member 232 may alternatively be a distinct component that is mechanically coupled to inner tubular 230 at fixed end 232a. In such alternative embodiments, lower member 232 may be coupled to inner tubular 230 by any suitable means including without limitation welding, pins, or combinations thereof. In addition, lower member 232 is preferably a relatively rigid structure that experiences minimal flexing and bending as it is advanced through tissue. Further, it should be appreciated that in the embodiment illustrated in FIGS. 9 and 10, no portion of lower member 232 is located at a radial distance (as measured perpendicularly from axis 250) greater than inner radius $R_1$ of outer tubular 210, even when device 200 is in the opened position.

Referring still to FIGS. 9 and 10, upper member 231 includes a fixed end 231a integral with inner tubular 230 and a cutting end 231b, including a cutting tip 233, that cuts through tissue as upper member 231 is advanced through tissue. Cutting tip 233 preferably has a sharpened or beveled edge defined by an acute angle α that is preferably between 20° and 45°.

In addition, upper member 231 is disposed at an angle θ with respect to lower member 232. When device 200 is in the fully opened position illustrated in FIGS. 9 and 10, angle θ is at a maximum, termed herein open angle $\theta_O$. In general, the angular separation of upper member 231 and lower member 232 results from the bending or flexing of upper member 231 in a resilient flexing region 235 near fixed end 231a. Specifically, when upper member 231 is manufactured, upper member 231 is shaped or plastically deformed at flexing region 235 so as to form open angle $\theta_O$. For an upper member 231 having a length between 0.5" and 1.0" (as measured from cutting tip 233 to fixed end 231a), open angle $\theta_O$ is preferably between 5° and 30°, and more preferably between 8° and 20°.

Although flexing region 235 defines the opened position of upper member 231, upper member 231 may be elastically flexed within or about flexing region 235. Thus, upper member 231 may be described as being biased to the opened position, i.e. upper member 231 tends to return to open angle $\theta_O$ whenever it is flexed to an angle θ that differs from open angle $\theta_O$.

As previously described, flexing region 235 is formed by plastically deforming, bending, or otherwise shaping upper member into the opened position shown in FIGS. 9 and 10. In alternative embodiments, upper member 231 may be a distinct component that is mechanically connected to inner tubular 230. In such alternative embodiments, flexing region 235 may be formed by a pivotal connection between upper member 231 and inner tubular 230 that is biased opened, such as by a spring or the like. Thus, although upper member 231 elastically bends or flexes at flexing region 235 in the embodiments described herein, flexing region 235 may also be described as a pivoting region.

Referring still to FIGS. 9 and 10, upper member 231 extends inward (toward axis 250) at a second angled or bent region 237, forming a tooth 239 near cutting end 231b. The amount or degree of bending at angled region 237 is defined by an angle ρ relative to axis 250. Angled region 237 preferably has an angle ρ between 10° and 30°, and more preferably between 12° and 25°. Further, angled region 237 preferably has a smoothly contoured outer surface to enhance the ability of distal end 260 to pass smoothly through tissue. In addition to its utility in excising tissue, the inclusion of angled region 237 extending radially beyond outer radius $R_3$ of outer tubular 210 offers the potential for improved fluoroscopic visualization, and hence control, of distal end 260 of device 200. For instance, under fluoroscopic visualization, angled region 237 may project beyond any shadowing generated by other portions of device 200, such as a handle attached to device 200, etc.

As best seen in FIG. 9, upper member 231 is preferably slightly longer than lower member 232. Thus, as upper member 231 and lower member 232 are preferably sized and shaped such that upper member 231 can "clamp down" and mate with lower member 232 when upper member 231 flexes about flexing region 235 toward lower member 232 in the direction of arrow 238. Specifically, as upper member 231 flexes toward lower member 232, tooth 239 moves toward and preferably ultimately engages free end 232b and cutting tip 234 of lower member 232. It is to be understood that as upper member 231 pivots or flexes about flexing region 235 in the direction of arrow 238, the angle θ between upper member 231 and lower member 232 decreases.

Figure 11:
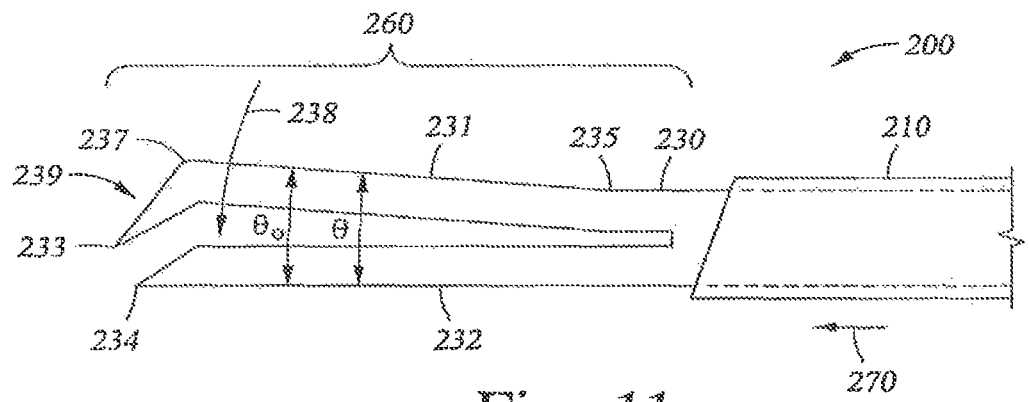
FIGS. 11-13 are series of side views of the tissue excision device illustrated in FIG. 9 transitioning from an open position to a closed position.
Figure 12:
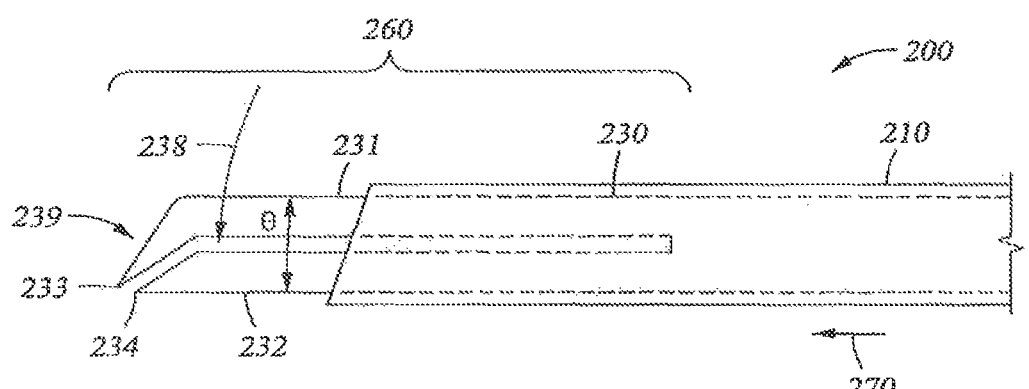
Figure 13:
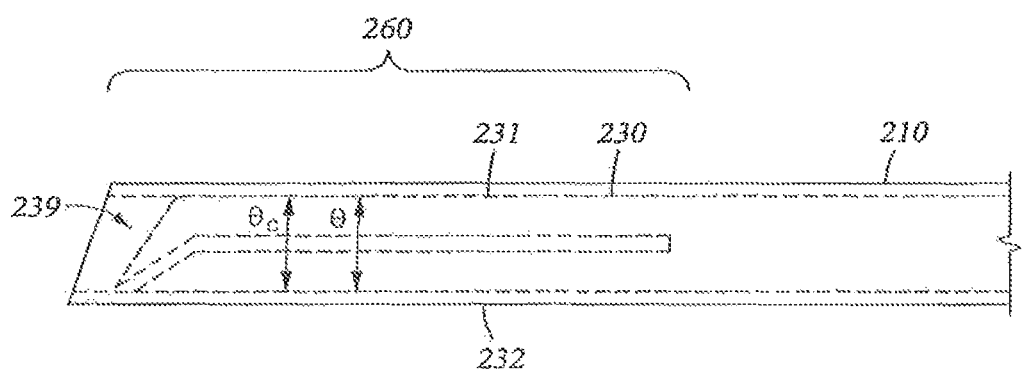

FIGS. 11-13 schematically illustrate the transition of tissue excision device 200 from the opened position (FIG. 11) to the closed position (FIG. 13). As shown in FIG. 11, tissue excision device 200 fully open. When device 200 is in the opened position, distal end 260 of inner tubular 230 is fully extended from outer tubular 210 and upper member 231 is biased away from lower member 232 and disposed at open angle $\theta_O$ relative to lower member 232. To close tissue excision device 200, outer tubular 210 is advanced toward distal end 260 generally in the direction of arrow 270. As outer tubular 210 advances over distal end 260, the inner surface of outer tubular 210 engages the outer surface of upper and lower members 231, 232, In particular, the inner surface of outer tubular 210 engages the portions of upper member 231 that extend radially beyond the inner radius $R_2$ of outer tubular 210. As a result, the inner surface of outer tubular 210 exerts a force on the outer surface of upper member 231, causing upper member 231 to elastically flex or pivot about flexing region 235 in the direction of arrow 238. Consequently, the angle θ decreases, as best seen in FIG. 12. As outer tubular 210 is advanced over distal end 260, upper member 231 continues move toward lower member 232. In FIG. 13, tissue excision device 200 has achieved a fully closed position. When device 200 is in the fully closed position, upper member 231 and lower member 232 are completely disposed within outer tubular 210 and angle θ between upper member 231 and lower member 232 is at a minimum, termed herein closed angle $\theta_C$. In particular, when device 200 is in the fully closed position, closed angle $\theta_C$ between upper member and lower member is preferably between 0° and 5°.

Figure 16:
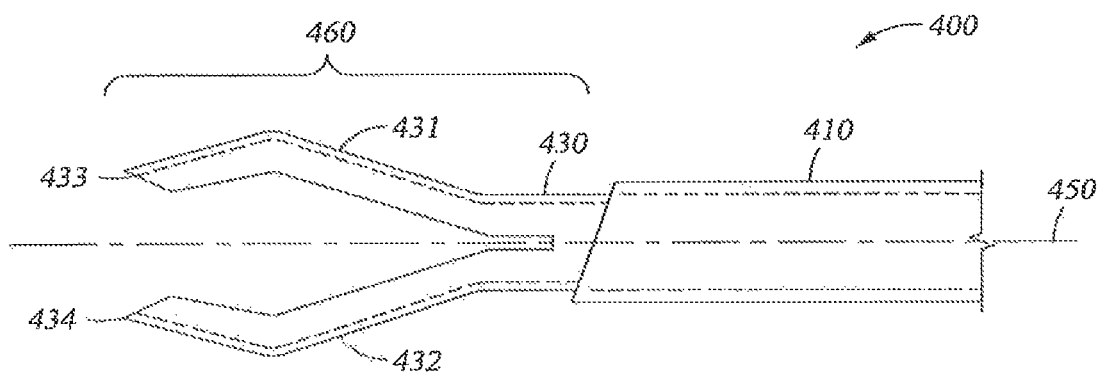
FIG. 16 is a perspective view of the distal portion of an embodiment of another tissue excision device in an open position.

Referring briefly to FIG. 16, another embodiment of a tissue excision device 400 is schematically illustrated. Like device 200, tissue excision device 400 comprises an inner tubular member 430 coaxially disposed within an outer tubular member 410. Inner tubular 430 includes a distal end 460 having an upper member 431 and a lower member 432. Upper member 431 includes a cutting tip 433 and lower member 432 includes a cutting tip 434. Device 400 operates substantially the same as device 200, with the exception that device 400 includes two movable members 431, 432 that each operate similarly to upper member 231 of device 200. When device 400 is in the opened position illustrated in FIG. 16, both upper member 331 and lower member 332 extend radially beyond the inner radius of outer tubular 410 (as measured from axis 450). When device 400 is actuated into the closed position, upper member 431 and lower member 432 are urged toward each other as outer tubular 410 advances over distal end 460.

Tissue Excision and Removal

Figure 14:
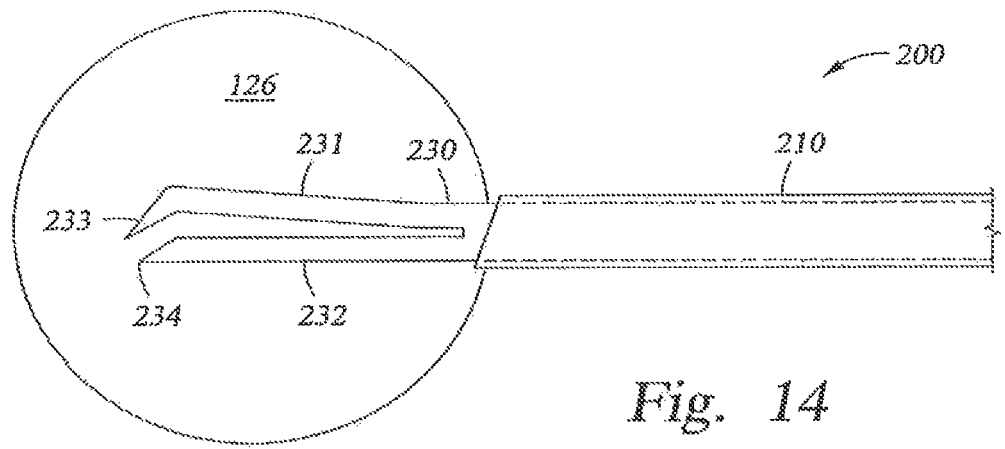
FIGS. 14 and 15 are sequential illustrations showing the excision of tissue by the tissue excision tool illustrated in FIG. 9.
Figure 15:
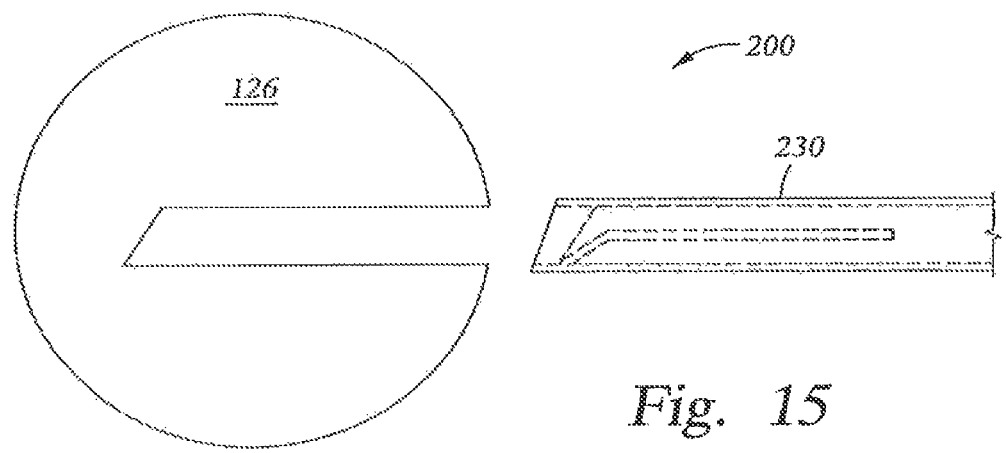

FIGS. 14 and 15 schematically illustrate the excision of a portion of tissue 126 by device 200. In some embodiments, a portal or cannula (not shown) may be employed to provide percutaneous access to tissue 126. For instance, tissue excision device 200 may be inserted into and advanced through such a portal or cannula to reach tissue 126. U.S. application Ser. No. 11/461,020 filed concurrently herewith, which is hereby incorporated herein by reference in its entirety, discloses several tools, devices and methods for employing a portal to provide percutaneous access to a tissue of interest. If a portal or cannula is used to guide device 200, device 200 may be passed through such cannula in the opened position or closed position.

Regardless of the manner in which tissue excision device 200 reaches the tissue of interest (e.g., by portal or otherwise), prior to insertion into the tissue to be excised, device 200 is configured in the opened position as shown in FIGS. 9, 11, and 14. With device 200 in the opened position, the distal portion of tissue excision device 200 is advanced into tissue 126, as best shown in FIG. 14. Tissue 126 may be any type of tissue to be excised and removed from a patient including without limitation, soft tissue, fat, muscle, or bone. When used to treat spinal stenosis caused by a thickened ligamentum flavum, distal end 260 of device 200 is preferably inserted into the stenotic ligamentum flavum 26, preferably posterior to a safety zone 40, in order to safely cut and remove portions of the thickened ligamentum flavum 26 (see FIGS. 2 and 3), thereby reducing the stenosis.

Still referring to FIGS. 13 and 14, as device 200 is inserted and advanced into tissue 126, cutting tips 233, 234 cut through tissue 126. In addition, as device 200 is advanced into tissue 126, portions of tissue 126 cut by cutting tips 233, 234 slide into and fill at least a portion of bore 240 of inner tubular 230. It is to be understood that the farther device 200 is advanced into tissue 126, the more tissue 126 is cut, and the greater the amount of cut tissue 126 that will occupy inner bore 240. Upper member 231, including flexing region 235 and angled region 237, as well as lower member 232 are preferably sufficiently rigid that the device does not inadvertently transition to the closed position as device 200 is advanced through the tissue. In other words, upper member 231 and lower member 232 are preferably sufficiently rigid and are configured such that the forces exerted on the outer surface of upper member 231 and lower member 232 by the surrounding tissue 126 as device 200 is advanced does not tend to move upper member 231 towards lower member 232.

In some embodiments, distal end 260 is shaped and configured such that the forces exerted on the inner surfaces of distal end 260 by tissue entering bore 240 are substantially balanced by the forces acting on the outside surfaces of distal end 260. In other embodiments, the distance perpendicular to axis 250 between cutting tip 233 and cutting tip 234 is 80% to 120% of the diameter of bore 240.

Once the desired amount of tissue has been cut by device 200 and disposed within inner bore 240, outer tubular 210 may be slid toward and over distal end 260, thereby closing device 200 as previously described. As upper member 231 and lower member 232 move towards each other, tissue 126 within bore 240 is severed from the surrounding tissue 126. For instance, tooth 239 and cutting tip 233 slice tissue extending axially from bore 240, and annular cutting edge 211 of outer tubular 210 slices tissue extending radially from bore 240 between upper member 231 and lower member 232. In some embodiments, cutting edge 211 of outer tubular 210 is sharpened or beveled to enhance the cutting ability of outer tubular 210. Once device 200 has achieved the closed position, device 200 may be retracted from tissue 126 as best shown in FIG. 15. The portion of tissue 126 contained within inner bore 240 is removed along with device 200. Once device 200, including a portion of tissue 126 within inner bore 240, has been completely removed from the patient, resected tissue within bore 240 is removed from bore 240 (i.e., bore 240 is emptied) so that device 200 may be reinserted into tissue 126 to continue to the cutting and removal of portions of tissue 126.

Pieces of tissue 126 captured within inner bore 240 may be removed by simply opening device 200 and pulling the pieces of tissue from inner bore 240. Device 200 may be opened from the closed position by retracting outer tubular 210 from inner tubular 230, thereby extending distal end 260 from outer tubular 210. As device 200 transitions to its opened position, upper member 231 and lower member 232 will separate and angle θ will increase, allowing the user to access inner bore 240. In preferred embodiment, once outer tubular 210 is sufficiently retracted, upper member 231 will retake its initial open position with angle η and angle θ at their respective maximums. In other words, upper member 231 is sufficiently rigid to rebound to its original opened position once outer member 210 no longer restricts the radial movement of upper member 231 (i.e., upper member 231 acts like a spring).

In an alternative embodiment, a plunger or tissue ejector may be included with device 200, 300 to physically eject the excised tissue 126 from inner bore 240. For instance, a plunger 372 (FIG. 10) may be included within device 200 to push cut tissue within inner bore 240 out through the openings in distal end 260. Such embodiments are described in more detail below.

The process of inserting device 200 into tissue 126 in the opened position, closing device 126, retracting device 200 in the closed position, opening device 200, emptying inner bore 240, and reinserting device 200 may be repeated until the desired amount of tissue 126 has been excised and removed. Referring briefly to FIG. 3, when device 200 is employed to remove portions of thickened ligamentum flavum 26, this process may be repeated until the spinal canal is adequately decompressed. Further, when device 200 is employed to remove portions of thickened ligamentum flavum 26, the tips 233, 234 of device 200 are preferably controlled to remain within ligamentum flavum 26 and not penetrate safety zone 40. Nonetheless, safety zone 40 is preferably provided so that even an inadvertent penetration into epidural space 27 by device 200 will not result in damage to the dural sac 32 or nerves 34.

The components of tissue excision device 200 (e.g., outer tubular 210, inner tubular 230, members 231, 233, etc.) may comprise any suitable material(s) including without limitation metals (e.g., stainless steel, titanium, etc.), non-metals (e.g., polymer, composites, etc.) or combinations thereof. The components of tissue excision device 200 are preferably manufactured from a durable biocompatible material such as titanium or stainless steel, but may alternatively be polymeric. In addition, members 231, 233 each preferably comprise a relatively rigid material(s) capable of maintaining their shape and configuration when inserted into and advanced through tissue. Further, upper member 231 preferably comprises a resilient material having the ability to be repeatedly flexed from its initial opened position to its closed position (e.g., by pivoting about flexing region 235) and vice versa without cracking or otherwise being damaged. Similarly, it is desirable that upper member 231 resume its initial opened position when device 200 is transitioned from closed to opened (e.g., as outer tubular 210 is retracted from distal end 260, thereby allowing distal end 260 to extend from outer tubular 210). Thus, it is also preferred that upper member 231 comprise a resilient material capable resuming its original configuration once external forces (e.g., force applied by outer tubular 210) are removed.

In addition, the components of tissue excision device 200 may be manufactured by any suitable methods. Examples of suitable methods include casting or molding, machining, laser cutting, EMD, or combinations thereof. In some embodiments, cutting edges or tips may be electro polished to for sharpening. The components of tissue excision device 200 may be assembled by any suitable method including without limitation welding, press fitting, or combinations thereof. Still further, the inner surface of inner tubular 230 may be roughened by knurling, sand blasting, bead blasting, plasma etching, or other suitable means to enhance the ability of inner bore 240 to enhance grasping and retention of excised portions of tissue.

Multi-Function Tool for Tissue Ejection

Figure 17:
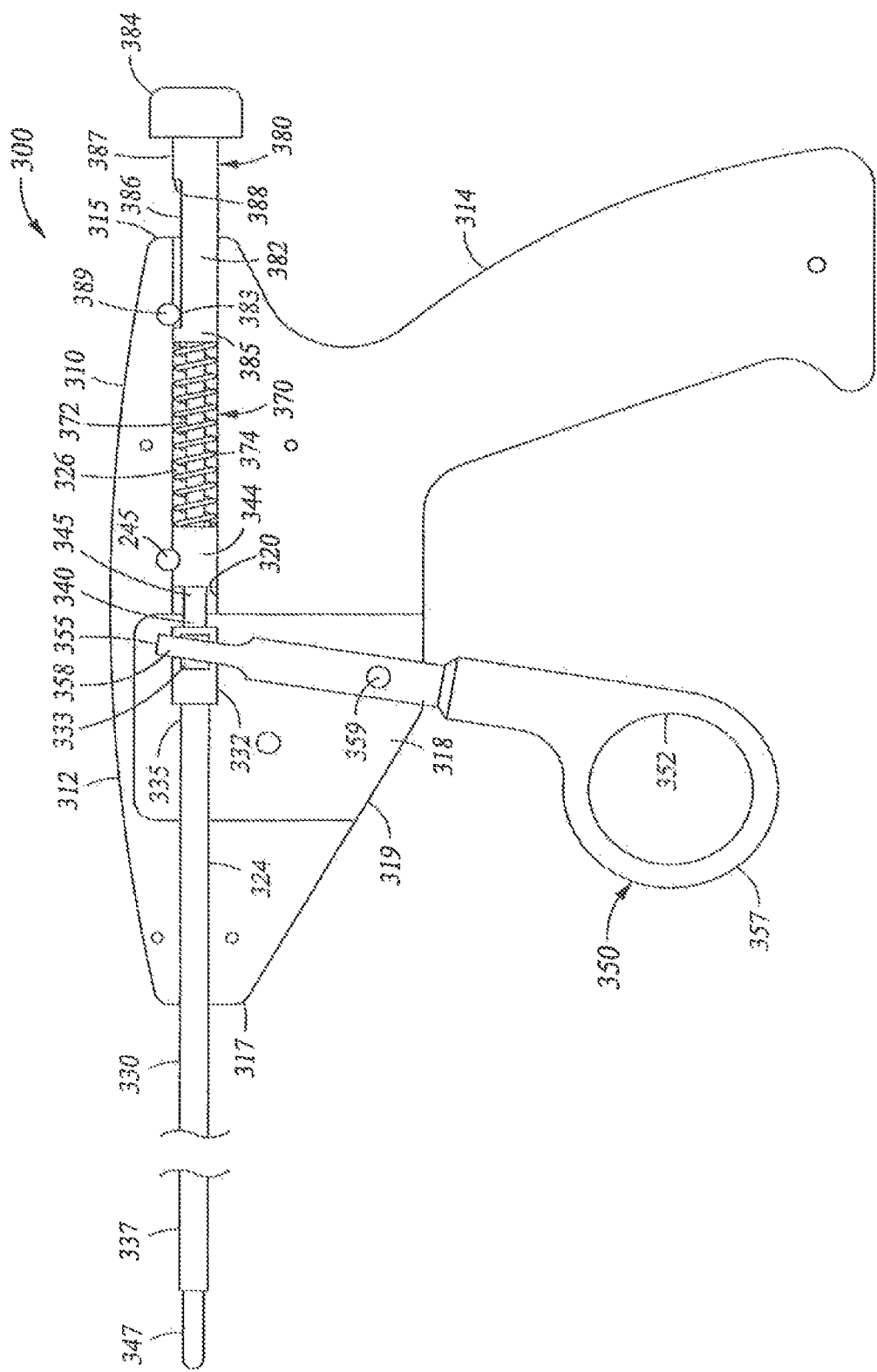
FIG. 17 is a partial cut-away view of an embodiment of a tissue ejection device.

Referring now to FIG. 17, the invention further includes a multi-function tool 300 that provides both tissue-resection and sample clearance. In certain embodiments, the multi-function tool supports one-handed operation, thereby increasing usability by the physician. Tool 300 generally includes a housing 310 having a bore 320 therethrough and a guide tube 330, trigger 350, and plunger 370 reciprocably disposed in bore 320. Housing 310 includes a body 312 with a grip 314 extending therefrom. Grip 314 is preferably ergonomically sized and shaped so that it can be easily and firmly grasped by a physician. Body 312 has a proximal end 315 and a distal end 317.

A trigger chamber 318 is disposed within body 312 and includes a trigger opening 319 adjacent to grip 314. Bore 320 preferably extends through housing 310 from proximal end 315 to distal end 317, intersecting trigger chamber 318. Bore 320 preferably includes a reduced diameter portion 324, which extends from distal end 317 to trigger chamber 318, and a larger diameter portion 326, which extends from trigger chamber 318 to proximal end 315.

Guide tube 330 is slidably received in bore 320. In some embodiments, guide tube 330 may be the same component as outer tubular 210 described above with regard to tissue excision device 200 (FIG. 10). Guide tube 330 is preferably sized so that its outer diameter is slightly less than the inside diameter of reduced diameter bore portion 324. Guide tube 330 has a proximal end 335 and a distal end 337. A sleeve 332 is preferably affixed to guide tube 330 at or near proximal end 335. Sleeve 332 preferably includes a trigger-engaging means 333 for engaging trigger 350, as described in detail below.

Disposed within guide tube 330 is a tissue-engaging means such as a tissue clamp 340. Tissue clamp 340 may be a rod 342 having a proximal end 345 and a distal end 347. In some embodiments, the distal end 347 may include a tissue excision device (e.g., tissue excision device 200) as described elsewhere herein. The proximal end 345 of tissue clamp 340 may include a stop 344 or other means for preventing movement of tissue engaging means 340 relative to body 312. Stop 244 may be rigidly affixed to tissue clamp 340 and may be held in place within body 312 by a pin 245. In alternative embodiments, proximal end 345 is held in place within body 312 by welding, pinning, crimping, or any other suitable means.

Trigger 350 has an inner end 355 and an outer end 357. Outer end 357 preferably includes a finger ring 352 or other similar ergonomic configuration that allows outer end 357 to be easily manually actuated toward grip 314. The inner end 355 of trigger 350 preferably includes at least one arm 358, which extends adjacent to and beyond guide tube 330. In preferred embodiments, arm 358 slidably engages trigger-engaging member 333 on guide tube 330. Trigger 350 is preferably pivotally mounted to housing 310 at a pivot point 359 between its inner and outer ends 355, 357. In certain embodiments, pivot point 358 is closer to inner end 355 than it is to outer end 357, so that a mechanical advantage can be employed during operation of the tool. A rotation stop 360 is preferably provided within cavity 318 and positioned so that it prevents rotation of inner trigger end 355 beyond a certain point.

In certain embodiments, tissue clamp 340 is provided as a hollow tube or rod. In these embodiments, it is preferred to provide a tissue ejection system 370. Tissue ejection system 370 may comprise yet another rod or tube 372 (also shown in phantom in FIG. 10), which is coaxial with and slidably disposed within tissue clamp 340. Rod 372 is initially positioned so that it extends out of the proximal end of tissue clamp 340 and its distal end 373 is disposed within tissue clamp 340 at a point that is slightly inward of the tissue resection means. Tissue ejection system 370 may include a plunger head 380 affixed to the proximal end of rod 372. Plunger head 380 preferably includes a plunger body 382 having distal and proximal ends 385, 387, respectively, and a knob or button 384 affixed to proximal end 387 of plunger body 382. A spring 374 or other biasing means is preferably mounted between the distal end 385 of plunger body 382 and stop 244.

In some embodiments, the outer surface of plunger body 382 preferably includes an offset portion 386 defined at its ends by distal and proximal shoulders 387, 388, respectively. A pin 389 is provided in body 312 and positioned so that it engages offset portion 386. While rod 372 is slidably within body 312, its axial movement in the distal direction is limited by engagement of pin 389 with proximal shoulder 388 and in the proximal direction by distal shoulder 387. Spring 274 is preferably configured such that it is slightly compressed when pin 389 engages distal shoulder 387. Thus, plunger head 380 is normally urged in the proximal direction so that it extends beyond the proximal end 315 of the device.

Operation of Multi-Function Tool

In operation, when it is desired to resect tissue from within a patient, the present multi-function tool allows a surgeon to remove a desired amount of tissue efficiently and precisely. In many instances, the tissue that is to be resected lies beneath the skin, and possibly within or adjacent to bone. For example, when stenosis is caused by hypertrophy of the ligamentum flavum, it may be desirable to remove portions of the hypertrophied ligament. In such cases, access to the resection site may be provided by inserting a trocar and cannula (e.g., instrument 101 in FIG. 8) through the skin and intervening soft tissue as described elsewhere herein. Once the tip of the device has reached the resection site, the trocar can be removed, leaving the cannula in place to serve as a portal to the site. In the case of a hypertrophied ligamentum flavum or other stenosis, it may be preferred to use an ipsilateral technique, as described elsewhere herein.

Figure 18:
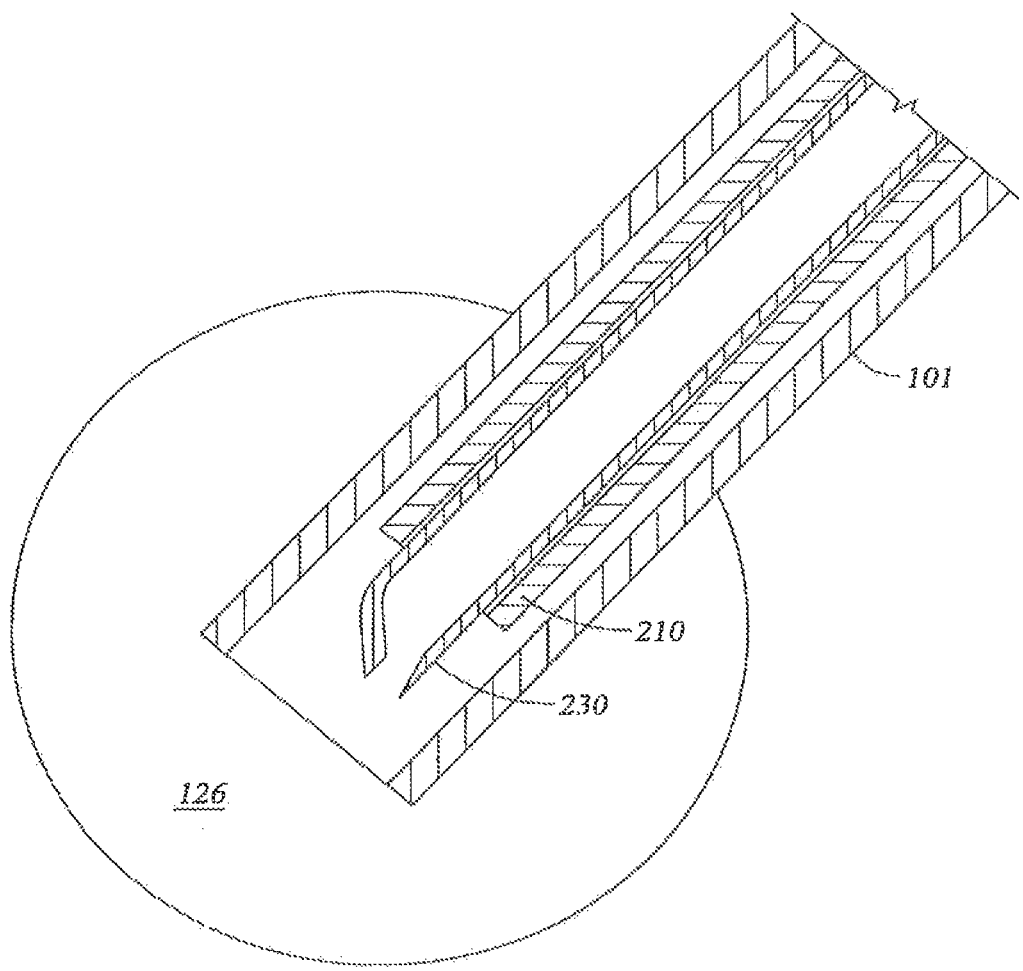
FIG. 18 is a schematic cross-section showing one embodiment of the present tool inserted into tissue via a cannula.

With the cannula in place, or not, the distal end of the present tool 300 is inserted to the resection site as shown in FIG. 18. Depending on the inner diameter of the cannula, the tissue excision device on the end of tool 300 may or may not be open as it passes through the cannula. Because the distal end 347 of tissue clamp 340 includes a tissue excision device (e.g., device 200 shown in FIG. 9) it will tend to engage, or "bite into" tissue as it advances out of the end of the cannula. When a desired amount of tissue has been engaged, up to the capacity of the excision device, that tissue can be resected by advancing guide tube 330 axially toward the distal end 347. As it advances, guide tube 330 bears on the outer surface of the tissue excision device (e.g., outer surface of upper member 231 shown in FIG. 10), urging the tissue excision device into a closed position. As the tissue excision device reaches the closed position, a segment of tissue is resected and retained within the tissue excision device (e.g., within bore 240 shown in FIG. 10). Guide tube 330 is advanced by applying pressure in the proximal direction on the outer end 357 of trigger 350. This causes trigger 350 to pivot around point 359, which in turn causes arm 358 to urge sleeve 332 in the distal direction. As sleeve 332 and tube 330 move in the distal direction, arm 358 pivots and shifts relative to sleeve 332. As the distal end 337 of the guide tube reaches the distal end 347 of the tissue clamp, it is prevented from advancing further by engagement with stop 360.

The closed tool 300, containing the segment of resected tissue, may then be pulled back, out of the cannula and emptied. To empty the tool 300, trigger 350 is urged distally, thereby causing guide tube 330 to retract into tool 300, which in turn allows the tissue excision device to open. Because it is not uncommon for the tissue segment to remain stuck within the device, tissue ejection system 370 may be used to discharge the tissue segment. Tissue ejection system 370 is actuated by applying pressure to knob 384, urging it in the distal direction. As it advances, plunger body 382 advances within the bore or lumen of the tissue excision device (e.g., bore 240 shown in FIG. 10), compressing spring 374. The distal end 373 of the plunger advances, pushing the tissue segment out as it does so. Once the tissue segment has been ejected, removing pressure from know 384 will allow spring 374 to return the plunger to its normal position, advancing rod 372 in the proximal direction until distal shoulder 387 bears on pin 380.

With the completion of these steps, tool 300 is ready to resect another tissue segment. It will be understood that the steps can be carried out in different sequences, depending on the desired objective. For example, tool 300 can be advanced to the desired resection site in a closed position, rather than an open position.

The ILAMP methods and techniques described herein allow spinal decompression to be performed percutaneously, avoiding the pain, lengthy recovery time, and risk associated with open surgery. In addition, the ILAMP methods and techniques described herein permit clearer, less obstructed imaging views of the interlaminar spaces and ligamentum flavum between the laminae in the areas of interest. Such improved imaging views offer the potential for enhanced accuracy and safety in the placement of tools within the ligamentum flavum proximal the epidural space and spinal cord. Further, the excision tools and devices described herein may be employed with the ILAMP methods, or alternative percutaneous methods, to excise portions of a thickened ligamentum flavum, thereby reducing spinal stenosis caused by such enlarged ligamentum flavum.

Through the provision of a safety zone and improved imaging, the present devices and techniques offer reduced risk of spinal cord damage. In addition to improving nerve function, it is expected that decompression of the spinal canal in the manner described herein will result in improved blood flow to the neural elements by reducing the extrinsic pressure on the spinal vasculature. For these reasons, it is believed that spinal decompression performed according to embodiments of the present invention will be preferable to decompression operations performed using currently known techniques.

While preferred embodiments of this invention have been shown and described, modifications thereof can be made by one skilled in the art without departing from the scope or teaching of this invention. For example, the means by which the safety zone is formed may be varied, the shape and configuration of the tissue excision devices may be varied, and the steps used in carrying out the technique may be modified. Accordingly, the invention is not limited to the embodiments described herein, but is only limited by the claims that follow, the scope of which shall include all equivalents of the subject matter of the claims. Likewise, the sequential recitation of steps in a claim, unless explicitly so stated, is not intended to require that the steps be performed in any particular order or that a particular step be completed before commencement of another step.

What is claimed is:

1. A medical device, comprising:
    a guide tube having a proximal end, a distal end, and a lumen extending from the proximal end to the distal end along a longitudinal axis of the guide tube, wherein the distal end includes an aperture having an elliptical shape angled from about 30 degrees to about 60 degrees relative to the longitudinal axis; and
    a tissue clamp including a monolithic tubular member having a distal region and a proximal region, wherein the proximal region is slidingly received in the lumen and the distal region has an upper member flexibly coupled to a stationary lower member, the upper member including a distal tip having a sharp edge angled towards the longitudinal axis and the lower member including a distal tip having a sharp edge fixed parallel to the longitudinal axis; and
    wherein, when the distal region is generally located outside of the lumen, the upper member is angled away from the longitudinal axis and the sharp edges of the upper and lower members are both positioned to at least partially cut tissue when the tissue clamp is moved along the longitudinal axis; and
    wherein, when the distal region is generally located within the lumen, the upper member is positioned generally parallel to the longitudinal axis and the sharp edges of the upper and lower members engage to generally close the aperture of the guide tube.

2. The medical device of claim 1, wherein the sharp edges of the upper and lower members are generally U shaped to form convex outer surfaces and concave inner surfaces extending laterally from the longitudinal axis.

3. The medical device of claim 2, wherein the sharp edges of the upper and lower members are beveled at an angle ranging from about 15 degrees to about 45 degrees relative to the longitudinal axis.

4. The medical device of claim 1, wherein the lower member is permanently positioned parallel to the longitudinal axis.

5. The medical device of claim 1, further including a sharp edge located about a periphery of the elliptical shape.

6. The medical device of claim 1, wherein, when the distal region is generally located within the lumen, the upper and lower members engage to form a blunt distal end of the tissue clamp that at least partially extends distally beyond the aperture of the guide tube.

7. A medical device, comprising:
    a guide tube having a proximal end, a distal end, and a lumen extending from the proximal end to the distal end along a longitudinal axis of the guide tube, wherein the distal end includes an aperture having an elliptical shape positioned at an angle relative to the longitudinal axis; and
    a tissue clamp including a unitary tubular member having a distal region and a proximal region, wherein the proximal region is slidingly received in the lumen and the distal region has an upper member moveably coupled to a lower member, the upper member being flexible and including a distal tip angled towards the longitudinal axis and the lower member being stationary and including a distal tip fixed parallel to the longitudinal axis; and
    wherein, when the distal region is generally located outside of the lumen, the upper member is angled away from the longitudinal axis and the upper and lower members are both configured to cut tissue when the tissue clamp is moved along the longitudinal axis; and
    wherein, when the distal region is generally located within the lumen, the upper member is positioned generally parallel to the longitudinal axis and a curved outer surface of a distal part of the upper member is substantially parallel to the angle of the aperture of the guide tube.

8. The medical device of claim 7, wherein an area of the curved outer surface is substantially similar to an area of the elliptical shape of the aperture of the guide tube such that the curved outer surface generally fills the aperture when the distal region is generally located within the lumen.

9. The medical device of claim 7, wherein at least part of the curved outer surface extends beyond the aperture of the guide tube to form a blunt distal end of the tissue clamp when the distal region is generally located within the lumen.

10. The medical device of claim 7, wherein the angle of the aperture ranges from about 30 degrees to about 60 degrees relative to the longitudinal axis.

11. A medical device, comprising:
a guide tube having a longitudinal axis, a distal aperture, a proximal end, and a lumen extending from the distal aperture of the guide tube towards the proximal end of the guide tube, wherein the distal aperture is angled relative to the longitudinal axis to form a leading edge and a trailing edge about a periphery of the distal aperture, and the leading edge is located distal to the trailing edge; and
a tissue clamp formed from a unitary tube having a distal end and a proximal end, wherein the tissue clamp is at least partially disposed within the lumen and is moveable along the longitudinal axis relative to the guide tube, the distal end of the tissue clamp including an upper member and a lower member, the upper member having a flexing region in a proximal end of the upper member, an angled region in a distal end of the upper member, and a medial region located between the flexing region and the angled region, and
wherein the flexing region is flexible and concave in a longitudinal direction to bend an outer surface extending longitudinally along the upper member away from the longitudinal axis about the flexing region, the angled region is rigid and convex in a longitudinal direction to bend the outer surface of the upper member towards the longitudinal axis about the angled region, and the trailing edge of the distal aperture is configured to engage the upper member of the tissue clamp to move the upper member towards the lower member.

12. The medical device of claim 11, wherein the lower member is fixed parallel to the longitudinal axis.

13. The medical device of claim 12, wherein the upper member includes a distal tip having a sharp edge angled towards the longitudinal axis and the lower member includes a distal tip having a sharp edge fixed parallel to the longitudinal axis.

14. The medical device of claim 13, wherein the trailing edge of the distal aperture is configured to engage the outer surface of the medial region to move the distal tip of the upper member towards the distal tip of the lower member.

15. The medical device of claim 14, wherein the trailing edge of the distal aperture is configured to engage the angled region to substantially close the distal aperture with the distal end of the upper member.

16. The medical device of claim 15, wherein the sharp edge of the upper member is configured to engage the sharp edge of the lower member when the trailing edge of the distal aperture engages the angled region of the upper member and the leading edge of the distal aperture engages the lower member.

17. The medical device of claim 13, wherein at least one of the distal tip of the upper member and the distal tip of the lower member is generally U shaped to form a convex outer surface and a concave inner surface extending laterally from the longitudinal axis.

18. The medical device of claim 17, wherein at least one of the sharp edge of the upper member and the sharp edge of the lower member is generally U shaped to form a convex outer surface and a concave inner surface extending laterally from the longitudinal axis.

19. The medical device of claim 11, wherein the medial region is generally linear along the outer surface of the upper member about the medial region.

20. The medical device of claim 11, wherein the distal aperture has an angle of about 45 degrees relative to the longitudinal axis.

21. The medical device of claim 20, wherein the periphery of the distal aperture includes a beveled edge.

22. The medical device of claim 11, wherein the angled region includes an inner surface that is concave along the longitudinal axis.

23. The medical device of claim 11, wherein the angled region includes an inner surface that is concave in a lateral direction.

24. The medical device of claim 23, wherein the inner surface is concave in a direction perpendicular to the longitudinal axis.

25. The medical device of claim 11, wherein the angled region includes an inner surface that is concave along the longitudinal axis and in a lateral direction.

26. The medical device of claim 11, wherein the angled region includes an outer surface that is convex in a lateral direction.

27. The medical device of claim 11, wherein the flexing region includes an inner surface that is convex along the longitudinal axis.

28. The medical device of claim 11, wherein the flexing region includes an inner surface that is concave in a lateral direction.

29. The medical device of claim 28, wherein the inner surface is concave in a direction perpendicular to the longitudinal axis.

30. The medical device of claim 11, wherein the flexing region includes an inner surface that is convex along the longitudinal axis and concave in a lateral direction.

31. The medical device of claim 11, wherein the flexing region includes an outer surface that is convex in a lateral direction.

32. A medical device, comprising:
a guide tube comprising a hollow, rigid, metal tube having a lumen extending along a longitudinal axis of the guide tube; and
a tissue clamp comprising a monolithic metal tube having a distal region and a proximal region, wherein the distal region includes an upper jaw member and a lower jaw member, the lower jaw member rigidly and fixedly extending parallel to the longitudinal axis, the upper jaw member being flexible and configured to close relative to the lower jaw member to at least partially cut tissue, and at least part of the proximal region is slidingly received in at least part of the lumen of the guide tube; and
wherein, when the distal region is generally located outside of the lumen, the upper member is angled away from the lower member and a sharp edge of the upper members is angled towards the lower member to cut tissue when the tissue clamp is moved along the longitudinal axis; and
wherein, when the distal region is generally located within the lumen, the upper member is angled generally parallel to the lower member to generally close a distal opening of the lumen.

33. The medical device of claim 32, wherein the upper member has a flexing region in a proximal end of the upper member and an angled region in a distal end of the upper member, wherein the flexing region is flexible and concave to bend an outer surface extending along the entire length of the outside of the upper member away from the lower member about the flexing region and the angled region is rigid and convex to bend the outer surface of the upper member towards the lower member about the angled region.

34. The medical device of claim 33, wherein the upper member further includes an inner surface extending along the entire length of the inside of the upper member, and the angled region is concave to bend the inner surface towards the lower member about the angled region.

35. The medical device of claim 33, wherein the tissue clamp, when the distal region is generally located within the lumen, includes an inner volume configured to receive a tissue sample, the inner volume extending from the angled region to at least the flexing region.

* * * * *